(12) United States Patent
Weinstein

(10) Patent No.: US 12,558,248 B2
(45) Date of Patent: Feb. 24, 2026

(54) CORRECTIVE APPARATUS FOR DEFORMED EXTERNAL EAR

(71) Applicant: EARGEAR, LLC, Brooklyn, NY (US)

(72) Inventor: Gila R. Weinstein, Brooklyn, NY (US)

(73) Assignee: EARGEAR, LLC, Brooklyn, NY (US)

( * ) Notice: Subject to any disclaimer, the term of this patent is extended or adjusted under 35 U.S.C. 154(b) by 246 days.

(21) Appl. No.: 18/021,616

(22) PCT Filed: Aug. 17, 2021

(86) PCT No.: PCT/US2021/046349
§ 371 (c)(1),
(2) Date: Feb. 16, 2023

(87) PCT Pub. No.: WO2022/040218
PCT Pub. Date: Feb. 24, 2022

(65) Prior Publication Data
US 2023/0301815 A1 Sep. 28, 2023

Related U.S. Application Data

(60) Provisional application No. 63/066,634, filed on Aug. 17, 2020.

(51) Int. Cl.
*A61F 5/058* (2006.01)

(52) U.S. Cl.
CPC ................................. *A61F 5/05891* (2013.01)

(58) Field of Classification Search
CPC ........ A61F 2/18; A61F 5/05891; A61F 11/00; A61F 11/06; A61F 11/11; A61F 11/20;
(Continued)

(56) References Cited

U.S. PATENT DOCUMENTS

| | | |
|---|---|---|
| 6,517,557 B1 | 2/2003 | Sorribes |
| 2012/0179078 A1 | 7/2012 | Koehler |

(Continued)

FOREIGN PATENT DOCUMENTS

| | | |
|---|---|---|
| GB | 2304579 A | 3/1997 |
| WO | 2018053219 A1 | 3/2018 |

OTHER PUBLICATIONS

International Search Report and Written Opinion for corresponding International Appl. No. PCT/US2021/046349 mailed Jan. 18, 2022 (17 pages).

(Continued)

*Primary Examiner* — Ophelia A Hawthorne
(74) *Attorney, Agent, or Firm* — Farber LLC

(57) ABSTRACT

A non-surgical corrective apparatus for a deformed external ear is described. The corrective apparatus may be worn externally to correct a deformity or malformation on the external ear through molding over a period of time. In one aspect, the corrective apparatus includes a corrective component configured for contacting a target surface of the external ear and maintaining a desired shape to reshape the deformity; and an attachment element configured for placement around a helix of the ear for remodeling the outer portion of the helix and securing the corrective component against the target surface. The attachment element is strong enough to maintain the corrective component in place during the time period of use and sufficiently atraumatic to avoid causing any harm or further deformities to the patient's ear during use or removal.

18 Claims, 20 Drawing Sheets

(58) Field of Classification Search
CPC .. A61F 5/00; A61F 5/01; A61F 5/0102; A61F
5/04; A61F 5/05; A61F 5/058; A61F
5/05883; A61F 11/08; A61F 11/085;
A61F 11/10; A61F 11/30; H04R 1/105;
H04R 25/02; H04R 25/652; H04R
25/656; H04R 5/0335; H04R 1/1008;
H04R 1/1016
See application file for complete search history.

(56) References Cited

U.S. PATENT DOCUMENTS

| | | | |
|---|---|---|---|
| 2015/0051639 A1* | 2/2015 | Case | A61F 5/0102 |
| | | | 606/204.15 |
| 2020/0146891 A1* | 5/2020 | Weinstein | A61F 5/01 |
| 2021/0145351 A1* | 5/2021 | Robertson | A61B 5/291 |

OTHER PUBLICATIONS

International Preliminary Report on Patentability for corresponding
International Appl. No. PCT/US2021/046349 dated Mar. 2, 2023,
11 pages.

* cited by examiner

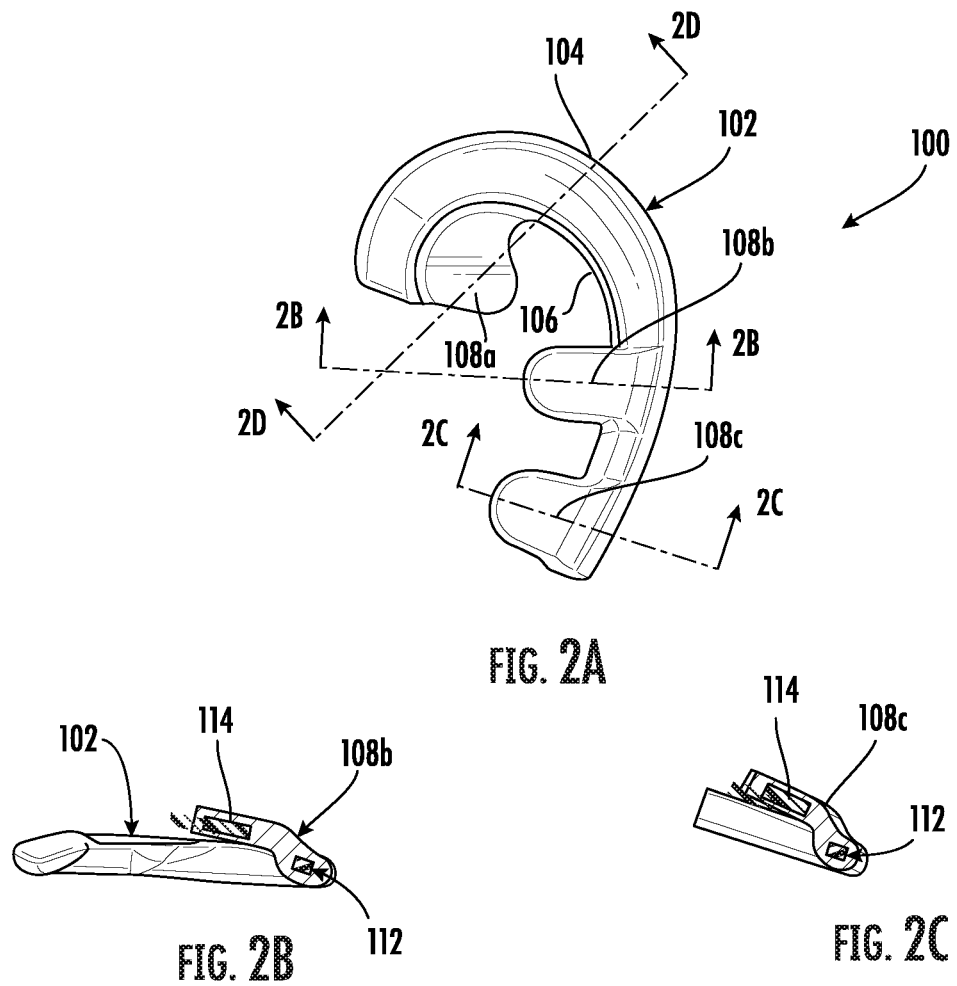
FIG. 2A
FIG. 2B
FIG. 2C
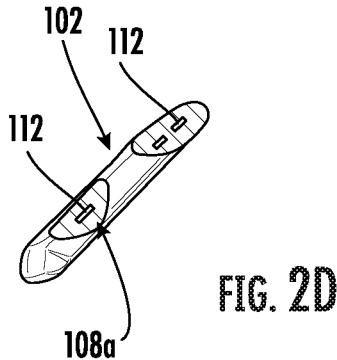
FIG. 2D

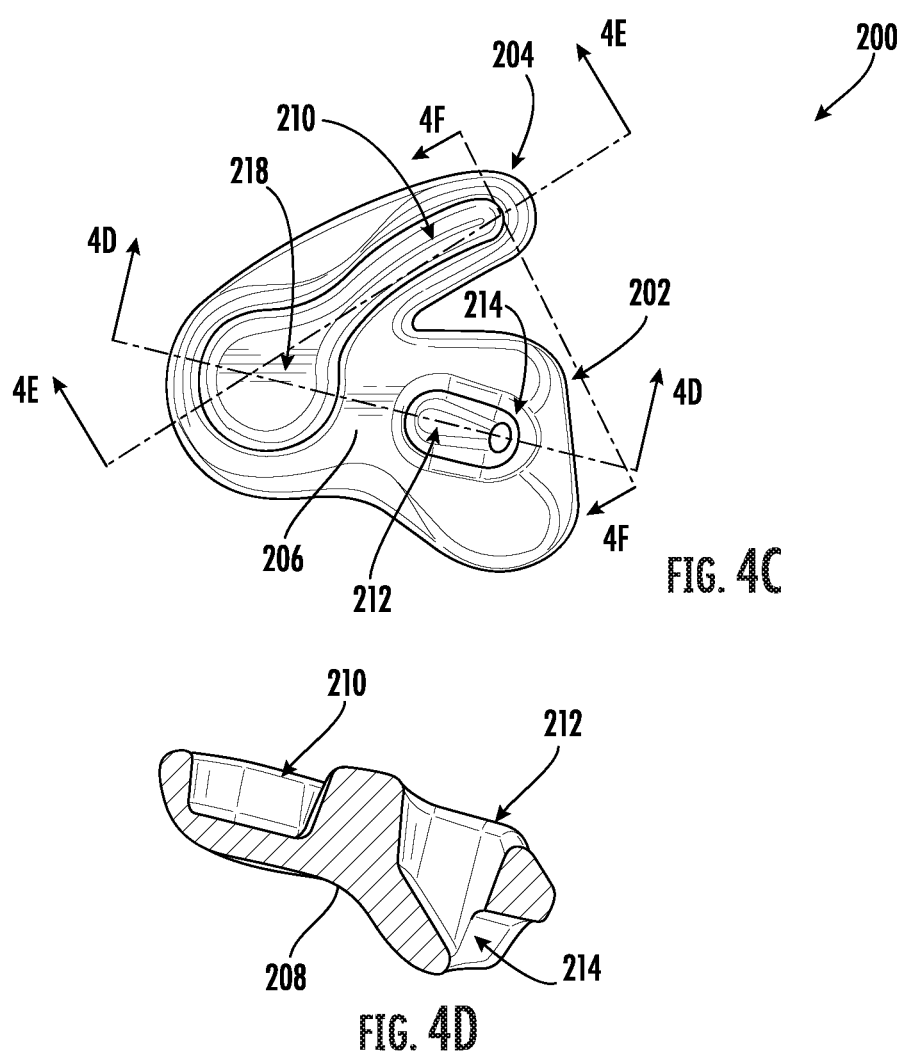
FIG. 4C
FIG. 4D
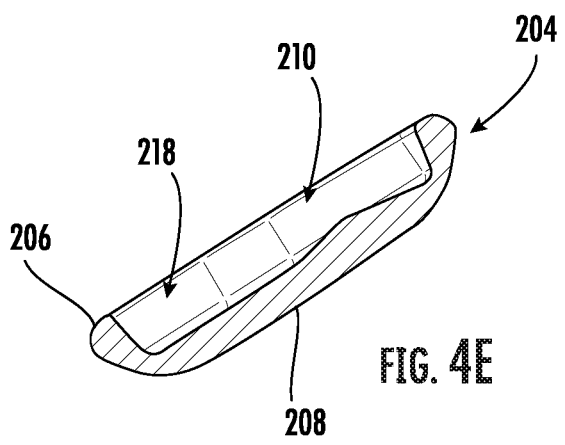
FIG. 4E

240

244

242

246

5B

5C

5C

5B

246

5B

252

242

246

252

246

252

250

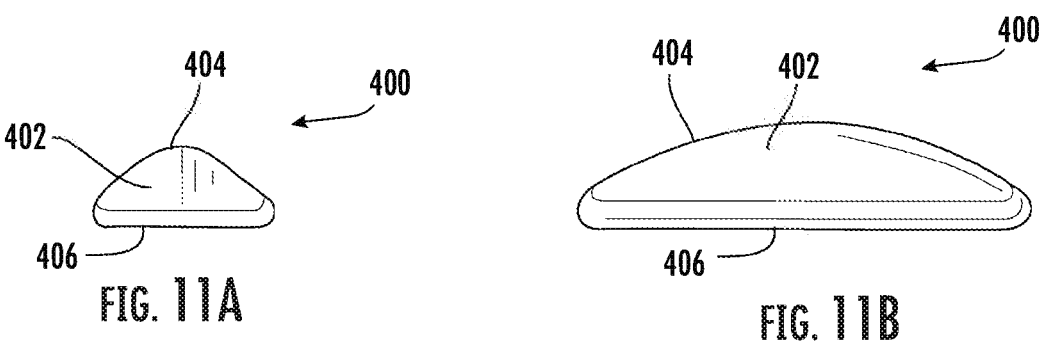
FIG. 11A
FIG. 11B
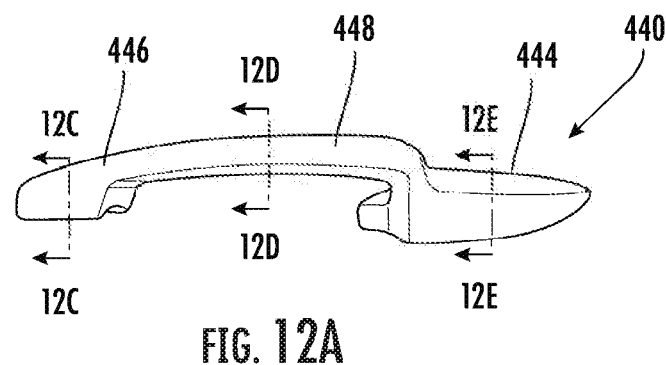
FIG. 12A
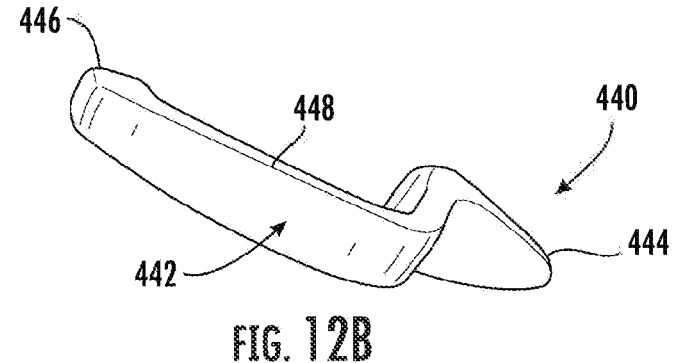
FIG. 12B
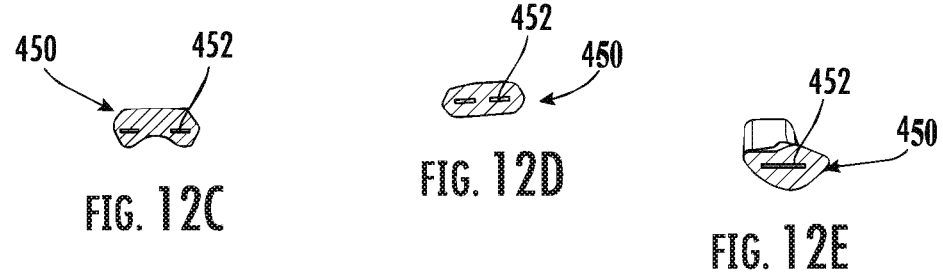
FIG. 12C
FIG. 12D
FIG. 12E 452
450
400
310
446

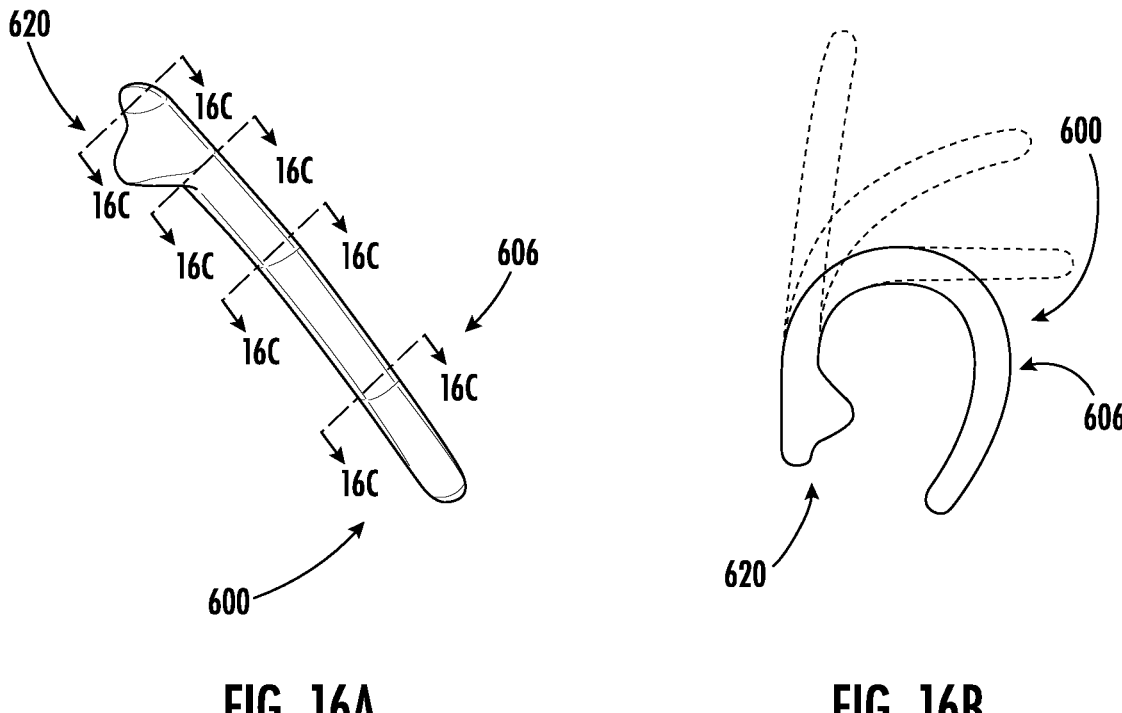
FIG. 16A
FIG. 16B
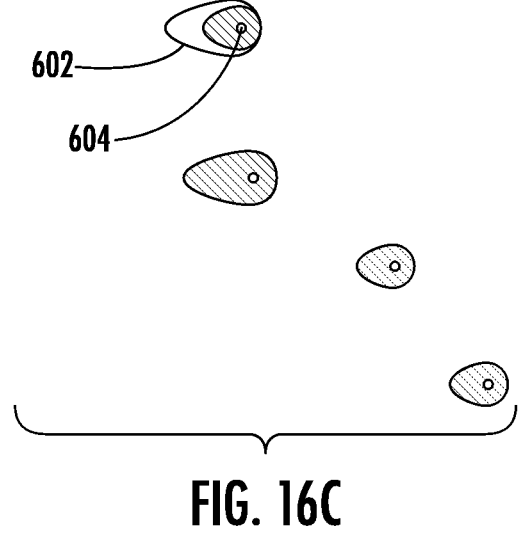
FIG. 16C

CORRECTIVE APPARATUS FOR DEFORMED EXTERNAL EAR

CROSS-REFERENCE TO RELATED APPLICATIONS

This application is the national phase entry of International Patent Application No. PCT/US2021/046349, filed on Aug. 17, 2021, which claims priority to U.S. Provisional No. 63/066,634, filed Aug. 17, 2020 and entitled "Corrective Apparatus for Deformed External Ear," the contents of both of which are hereby incorporated in their entireties by reference.

FIELD

The present disclosure relates to a non-surgical corrective apparatus for a deformed external ear. The corrective apparatus may be worn externally to correct a deformity or malformation of the external ear through molding or reshaping over a period of time.

BACKGROUND

The external ear is an important biological structure that aids in human hearing. In newborns, the external ear can be deformed. When infants are born with an irregular ear shape, they are said to have congenital auricular deformity. This can range from an auricular deformity (an abnormally shaped ear) with no missing tissue, to a malformation (missing tissue), to microtia (the external ears are not fully developed).

Various portions of the ear can be deformed, malformed or missing entirely. Common ear deformities include a Stahls deformity (often referred to as a Spock ear), a lop ear (i.e., the helical rim is folded over covering a portion of the antihelix) or a cryptotia, wherein a portion of the top of the ear is under the temporal scalp skin. An external ear deformity can cause a range of issues from cosmetic abnormalities to hearing and functional problems. Functional problems may include a variety of complications, such as difficulty wearing a hearing aid when there is a blocked ear canal. Only a small percentage of such deformities self-correct within the first week or two of life. Following the neonatal stage, an ear deformity may require surgery to correct.

External ear shaping mechanisms are known. For example, U.S. Pat. No. 7,850,702 provides a clamp in the form of a mainly U-shaped or V-shaped device that serves to non-invasively affect a cartilage fold on, for example, the exterior ear, by exerting a stretching and compressive force. U.S. Pat. No. 9,023,105 provides a system and method for correcting misshaped ears using a molding device having one or more braces supporting a scaphal mold. International Patent Application Publication No. WO 2014/167381 provides a preformed expander implant for ear reconstruction, using a reconstruction method which involves expanding autologous (the patient's own) tissues, and ideally performed in one surgical operation.

As noted, various systems and methodologies for correcting external ear deformities are known in the art. However, these existing systems are not specifically customized for use on a newborn or young infant patient, who have unique needs due to the delicate nature of their skin in addition to the smaller space for treatment. Some of the systems are configured to adhere to the patient's skin, and would be potentially harmful if used for extended periods of time on a young patient whose skin is particularly fragile. Other systems exert too much physical force against the young patient's ear, causing unnecessary pain. Still others are not sized appropriately and/or are too heavy for younger patient's ears, and either do not provide the desired results, or worse, create further problems when worn over time such as malformations arising from the treatment itself. These conventional devices fail to solve all the problems that are overcome by the present disclosure. Embodiments of the invention are presented in the drawings below and will be described in more detail herein.

SUMMARY

The present disclosure provides a non-surgical corrective apparatus for a deformed external ear. The corrective apparatus may be worn externally to correct a deformity or malformation on, or within, the external ear through molding over a period of time. The corrective apparatus may be configured for use with an external ear of a newborn or young infant. Using a typical infant's ear as a guide, the corrective apparatus is configured to mold and reshape the deformed ear and correct its present deformities. The corrective apparatus may be used in combination with an additional external ear component, and/or as part of a corrective system to treat multiple areas the ear.

In one exemplary embodiment of the present disclosure, a corrective apparatus for treating a deformity of an external ear is provided. The corrective apparatus includes a corrective component configured for contacting a target surface of the external ear sufficient to maintain a desired shape to reshape the deformity, and an attachment element configured for placement around a helix of the ear for securing the corrective component against the target surface. The attachment element is rigid enough to maintain the corrective component in place during the time period of use, while being sufficiently atraumatic to avoid causing any harm or further deformities to the patient's ear during use or removal.

In certain embodiments, the attachment element comprises a main body shaped for contacting at least a portion of the corrective component and one or more elongate members extending away from the main body. The elongate members are preferably configured to wrap around at least a portion of the helix of the ear to secure the corrective component in place.

In an exemplary embodiment, the attachment element includes a relatively atraumatic outer portion for contacting the ear and an inner portion embedded therein for maintaining a shape of the outer portion. The inner portion is bendable such that the elongate members can be wrapped around the helix, while having sufficient rigidity to remain in place during a time period of use sufficient to correct the deformity. The outer portion may comprise any suitable soft, atraumatic material for placement against the skin of an infant, such as silicone, polymer, plastic or a blend thereof. The inner portion may comprise any suitable bendable, but substantially rigid, material, such as a metal or rigid polymer wire, flexible thread or rod, wire mesh and the like.

In one embodiment, the corrective component comprises a main body shaped to substantially conform to the triangular fossa and the inner helical rim of the ear for correcting a deformity of the helix. The attachment element comprises a main body having an arcuate shape corresponding to the desired or "model" shape of the helix and one or more inner projections extending from the main body. The inner projections are preferably configured to facilitate alignment between the corrective component and the attachment element and to help secure the corrective component against the inner surface of the external ear. The corrective component may also include one or more flanges shaped to correspond with the one or more inner projections of the attachment element.

In another embodiment, the corrective component is shaped for insertion into a conchal bowl of the ear. This corrective component comprises a main body configured for placement in the concha cavum and a stem extending from the main body and configured for placement in or around the concha cymba of the external ear. The conchal bowl corrective component is configured to remodel the conchal bowl into the desired or model shape. In an exemplary embodiment, this corrective component includes a first surface, a second opposing surface and a hole extending through the first and second surfaces for passing sound waves therethrough. Providing this through hole allows the infant to hear sounds unimpeded, while wearing the corrective component.

In yet another embodiment, the corrective apparatus comprises a second corrective component configured for contacting a surface of the external ear. In this embodiment, for example, the corrective components may include one shaped for the inner surface of the helix and one shaped for the conchal bowl of the ear. The attachment element may include one or more flanges or projections extending inwardly from the main body. The flanges are sized and configured to facilitate alignment with the first and second corrective components during installation of the apparatus and to help secure the corrective components in place during use.

In one method according to the present disclosure, a corrective component, such as either the conchal bowl component or the helix component described above, is placed into contact with a target surface of the patient's external ear. The attachment element is aligned with certain portions of the corrective element. The elongate members of the attachment element are then wrapped around the helix of the patient's ear to secure the apparatus in place.

In another aspect of the disclosure, a corrective apparatus for treating a deformity of an external ear is provided. The corrective apparatus comprises a corrective component having a main body configured for contacting a target surface of the external ear sufficient to maintain a desired shape to reshape the deformity, and an attachment element having a main body and at least one inner portion within the main body. The inner portion is sufficiently bendable for movement into a position against the external ear to secure the corrective component against the target surface. The inner portion is also rigid enough to remain in position during a time period of use sufficient to correct the deformity.

The main body of the attachment element preferably includes an outer portion comprising a substantially atraumatic material, such as silicone, polymer, plastic or a blend thereof, to protect the infant's ear from trauma during installation and use. The inner portion preferably comprises a semi-rigid and bendable wire, filament, mesh or similar material embedded in the outer portion to allow for molding of the outer portion into the desired position against the patient's ear. The inner portion may be a continuous wire that extends through the attachment element, or it may comprise a plurality of discrete members dispersed throughout the attachment element. The discrete elements may be attached to each other, or separately embedded in the corrective element.

In certain embodiments, the attachment element comprises one or more external projections or fingers that extend away from the main body. The inner rigid portion preferably extends through the main body and the external projections. The attachment element may further comprise one or more flanges that extend in an opposite direction from the fingers to align the attachment element with the corrective component during installation.

In yet another aspect of the invention, a corrective apparatus for treating a deformity of an external ear comprises a corrective component having a main body configured for contacting a target surface of the external ear to maintain a desired shape to reshape the deformity, and an attachment element configured for securing the corrective component against the target surface. The main body comprises a first surface, a second opposing surface and a hole extending through the first and second surfaces for passing sound waves through the main body. The hole may be placed near, or over, the patient's ear canal to allow the patient to hear sounds while wearing the corrective apparatus.

In certain embodiments, the corrective component is shaped for insertion into a conchal bowl of the ear. The corrective component may comprise a stem extending from the main body and configured for placement against the cymba of the ear, while the main body is configured for placement against, or within, the cavum. In an exemplary embodiment, the stem may include an elongate channel extending through one surface that provides flexibility of movement of the stem during installation and/or use.

In yet another aspect of the invention, a corrective component for treating a deformity of an external ear comprises an outer portion configured for contacting a target surface of the external ear, and an inner portion that is sufficiently bendable for movement into a position against the external ear to secure the outer portion against the target surface. The inner portion is also rigid enough to remain in position during a time period of use sufficient to correct the deformity. In this embodiment, the corrective component is configured to remain in the patient's ear without the need for a separate attachment element. This further reduces any trauma or damage to the patient wearing the corrective component.

In certain embodiments, the main body has an arcuate shape to conform to an inner surface of the helix of the ear. In other embodiments, the main body is shaped for insertion into a conchal bowl of the ear.

In another aspect, a corrective apparatus for treating a deformity of an external ear comprises a corrective component shaped for insertion into a conchal bowl of the ear. The corrective component comprises a main body configured for positioning near, or in contact with, at least a portion of a cavum of the ear and a stem extending from the main body and being configured for positioning near, or in contact with, at least a portion of a cymba of the ear.

In certain embodiments, the stem of the corrective component includes a first surface, a second opposing surface and a cavity formed within the first surface. The cavity may be a substantially elongate channel extending through a portion of the stem. The cavity functions to provide additional flexibility to the stem such that it can be deformed slightly to fit within the conchal bowl of an infant ear. The cavity may also allow the stem to deform slightly during movement of the infant's ear, thereby providing more comfort and less trauma during use.

In certain embodiments, the main body includes a first surface, a second opposing surface and a cavity formed in the first surface. The main body further comprises a hole extending from the second opposing surface to the cavity in the main body, wherein the hole is substantially aligned with an ear canal for passing sound waves through the main body to the ear canal. The cavity in the main body may be configured to form an acoustic chamber around the hole to enhance the passage of sound waves therethrough.

The corrective apparatus may further comprise an attachment element configured for placement around a portion of the external ear for securing the corrective component against the conchal bowl. The attachment element may be secured to an outer skin surface of the patient's head. In addition, or alternatively, the attachment element may be configured to wrap around a helix of the ear.

In some embodiments, the main body and the stem of the corrective component may each comprise an outer portion configured for contacting a surface of the conchal bowl and an inner portion within the outer portion, wherein the inner portion is sized and shaped for placement within the conchal bowl to secure the outer portion against the conchal bowl, and is sufficiently rigid to remain in position during a time period of use sufficient to correct the deformity. This configuration may allow the corrective component to remain in place against the conchal bowl without requiring a separate attachment element. The outer portion of the main body and the stem preferably comprise a silicone, polymer, plastic, or a blend thereof. The inner portion may be sufficiently bendable for movement into a position against the conchal bowl.

In still another aspect, a kit for treating a deformity of an external ear is provided. This kit may include a corrective apparatus and corrective system as previously described. In addition, the kit may include a guide for determining which of the corrective apparatuses or corrective system to select for treating the deformity. This guide may comprise a transparency having an outline of a model human ear thereon. The outline of the model human ear may contain sections corresponding to at least one of the corrective apparatuses or corrective system. The sections may be designated by lines, and/or also may be color coded.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 2A is a front view of a corrective component for a helix of the ear according to the present disclosure;

FIG. 2B is a cross-sectional view of the corrective component of FIG. 2A taken along lines 2B-2B;

FIG. 2C is a cross-sectional view of the corrective component of FIG. 2A taken along lines 2C-2C;

FIG. 2D is a cross-sectional view of the corrective component of FIG. 2A taken along lines 2D-2D;

FIG. 4A;

FIG. 4D is a cross-sectional view of the corrective component of FIG. 4C taken along lines 4D-4D;

FIG. 4E is a cross-sectional view of the corrective component of FIG. 4C taken along lines 4E-4E;

FIGS. 11A and 11B illustrate side and front views, respectively, of another corrective component for use on a rear surface of the human ear according to the present disclosure;

FIGS. 12A and 12B illustrate side and perspective views, respectively, of an attachment element for the corrective component of FIGS. 11A and 11B;

FIGS. 12C-12E illustrate cross-sectional views of the attachment element of FIG. 12A along taken along lines 12C-12C, 12D-12D and 12E-12E, respectively.

FIGS. 16A-16C illustrate another embodiment of an attachment element according to the present disclosure.

DETAILED DESCRIPTION

The present disclosure provides a non-surgical corrective apparatus for a deformed external ear. The corrective apparatus may be worn externally to correct a deformity or malformation on the external ear through molding over a period of time. Using a typical infant's ear as a guide, the corrective apparatus is configured to mold and reshape the deformed ear and correct its present deformities. The corrective apparatus may be used in combination with an additional external ear component, and/or as part of a corrective system to treat the ear.

Figures 1A, 1B:
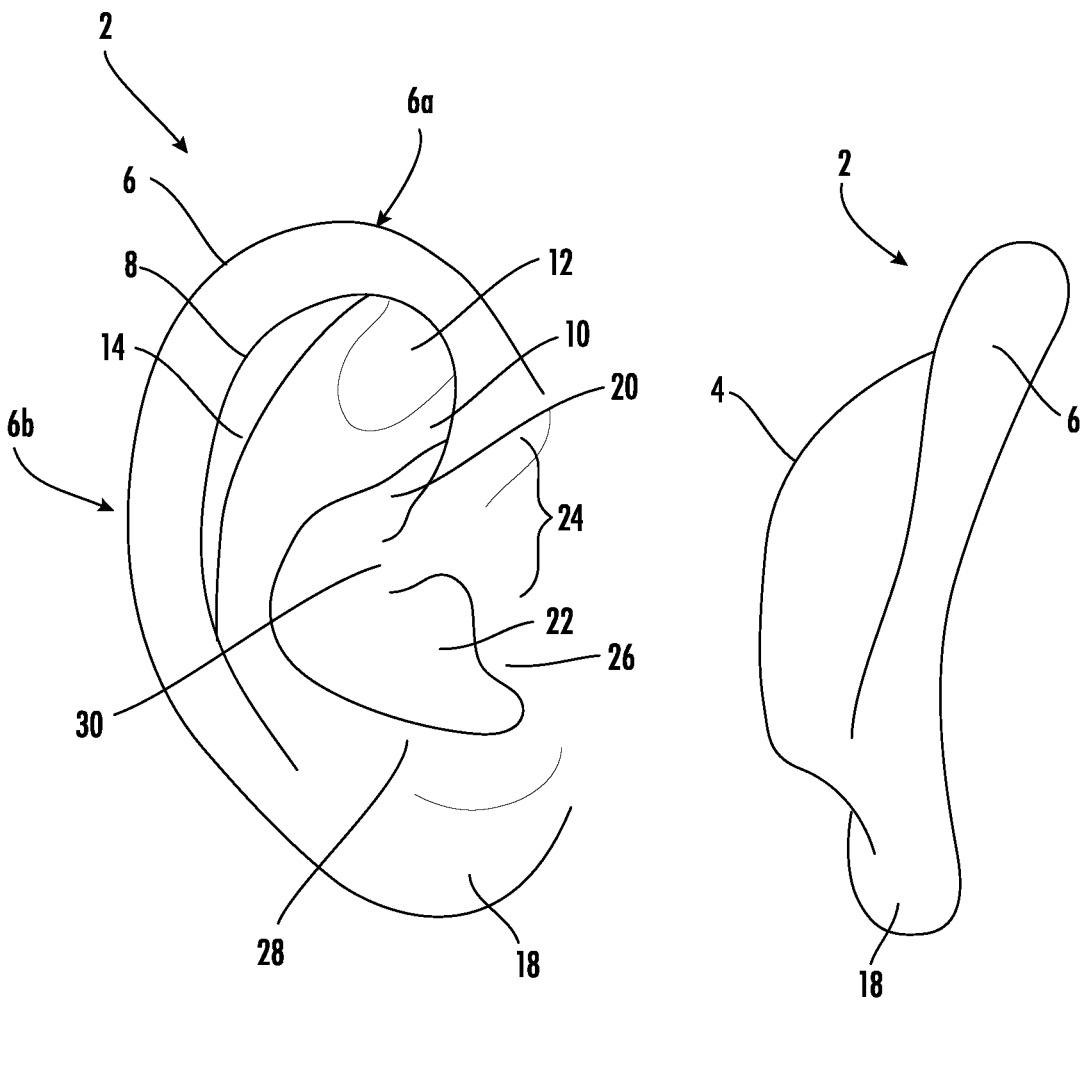
FIG. 1A shows a front view of an exemplary human right ear.
FIG. 1B shows the ear of FIG. 1A from a side view.

FIGS. 1A and 1B illustrate a normal human ear. The figures may be referred to for anatomical context and perspective to appreciate and understand the corrective apparatus of the present disclosure. In general, the visible part of the external ear is called the auricle. The auricle is also referred to as the pinna. The auricle is composed of a thin plate of cartilage. The cartilage is covered with skin. The cartilage is also connected to the surrounding parts by ligaments and muscles. Furthermore, the cartilage is connected to the commencement of the ear canal by fibrous tissue.

FIG. 1A shows a front view of a right ear 2 and FIG. 1B shows the ear 2 from a side view. The human ear 2 extends from a base 4 that attaches to the scalp skin (not shown). The major outer curved portion of the ear 2 is generally referred to as the helix 6. The helix 6 extends from a superior helix 6a to a descending helix 6b, as indicated in FIG. 1A. The ear 2 also includes a helical rim 8 and an antihelix 10 within the interior of the external ear 2 itself, as shown in FIG. 1A. The scapha 14 is the space between the helical rim 8 and the antihelix 10. The triangular fossa 12 is located at the upper inner portion of the ear 2. The ear 2 also includes the cymba 20 and cavum 22, which collectively can be generally referred to as the concha, or conchal bowl 24. Outside the conchal bowl 24 is the tragus 26 and antitragus 28, while the crus 30 is located between the cymba 20 and the cavum 22 of the conchal bowl 24. The bottom of the ear 2 extends into a lobule, or lobe 18, as shown in FIGS. 1A and 1B.

As mentioned, infants are sometimes born with external ear deformities or malformations, and external ear shaping mechanisms are known to exist. However, these existing ear shaping mechanisms do not always adequately address the unique concerns of newborns or young infants. For example, an ideal external ear remodeling mechanism would take into account the delicate skin of newborns, and avoid causing any harm or further deformities. Since the newborn and young infant ear is much smaller in scale than a normal human adult, the ear shaping mechanism needs to be appropriately sized as well as scaled (i.e., not too bulky or heavy) to be an effective treatment for a newborn and young infant.

The present disclosure provides various embodiments of corrective apparatuses configured to conform a shape of the deformed external ear of a newborn or infant to a shape of a model external ear when worn over a time period. In some embodiments, the corrective apparatus may be used in combination with an additional external ear component, and as part of a corrective system to treat the external ear deformity. In use, the corrective apparatuses or corrective systems act as a remodeling guide, enveloping and applying compression or exerting pressure on the ear deformity while also providing a physical support within its inner walls. The inner walls or sidewalls create a track to guide the remodeling process and to support the remodeled ear to maintain the desired shape. It is to be understood that what is meant by the term "remodeling" throughout this disclosure is the correction of the shape of the ear deformity.

These corrective apparatuses and corrective systems may be made from a medical grade silicone, polymer, plastic, polymeric blend, or similar soft and pliable material suitable for human use. In some embodiments, the material may be transparent, translucent, or semi-opaque, and allow the physician to see the patient's ear through the apparatus or system during use to monitor progress. The corrective apparatuses may also be formed of a metal material as well. The metal material may be coated or embedded within a polymeric or plastic coating or layer to further ensure that a smooth and non-damaging surface is provided for the patient.

Figure 2E:
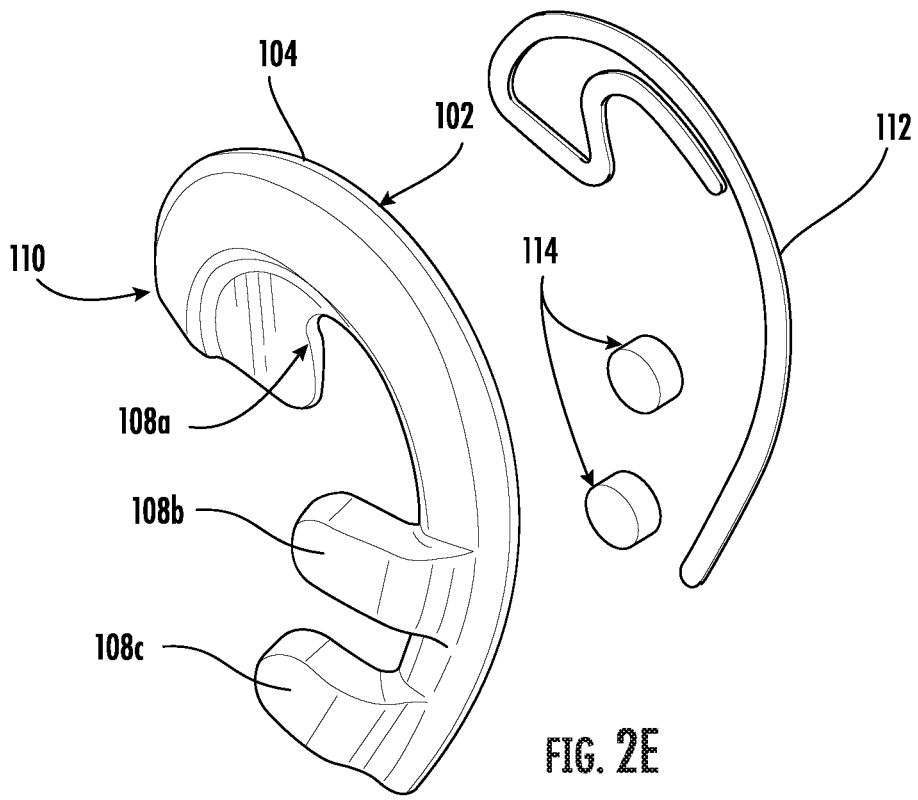
FIG. 2E is an exploded view of the corrective component of FIG. 2A.

Turning now to the drawings, FIGS. 2A to 2E illustrate various views of an exemplary embodiment of a corrective component 100 of the present disclosure for remodeling a deformed external ear into a model, or normal, external ear. FIG. 2A shows a front view of the corrective component 100, FIGS. 2B-2D show cross-sectional views along lines 2B-2B, 2C-2C and 2D-2D, respectively, and FIG. 2E shows an exploded view.

Figure 6A:
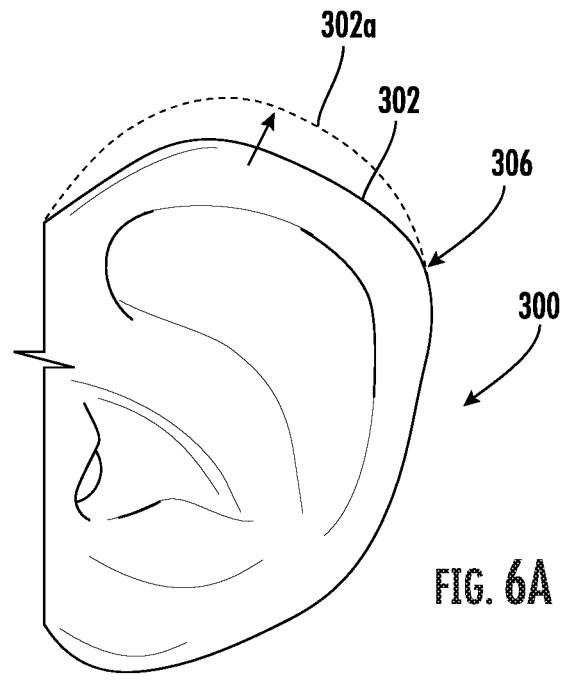
FIGS. 6A-6D illustrate the placement of the corrective component of FIG. 2A and the attachment element of FIG. 3A near, or against, the helix of an exemplary human ear according to the present disclosure.

Corrective component 100 may include a main body 102 for placement within, or in contact with, a portion of the helix 6 of the ear 2. In certain embodiments, main body 102 may be placed at least partially in contact with the scapha 14 below the helical rim 8 in order to remodel or reshape the helix 6 and create or widen the schapa as needed, as shown in FIG. 6A. As shown in FIG. 2A, the main body 102 preferably includes a generally convex outer surface 104 and a generally concave inner surface 106 designed to allow main body 102 to nest within helical rim 8 (see 6B). Corrective component 100 further includes one or more flanges or projections 108a, 108b, 108c extending inwardly from main body 102. Flanges 108 provide additional support for main body 102 within the patient's ear and also provide structure for aligning corrective component 100 with various attachment elements (discussed below). Flanges 108a may also serve to remodel the patient's ear with a desired triangular fossa shape. In use, the corrective apparatus 100 may be placed within the deformed helix 6 of the newborn or young infant for a time period sufficient to allow the deformed ear to remodel.

In an exemplary embodiment, corrective component 100 includes three flanges (108a, 108b and 108c) with the upper flange 108a generally defining a substantially triangular-shaped piece with three-dimensional rounding of the triangle downward that projects inwards relative to the curvature of main body 102 and the lower flanges 108b and 108c generally defining elongate fingers or projections that extend inwardly from main body 102. Of course, other configurations are possible. For example, corrective component 100 may include any combination of flanges 108a, 108b, 108c (e.g., only flanges 108a and 108c or only flanges 108a and 108b, etc.). Alternatively, main body 102 may not include any flanges 108.

As shown in FIG. 2E, main body 102 preferably comprises an outer portion 110 that comprises a flexible, soft and conformable material, such as medical grade silicone, polymer, plastic, polymeric blend, or similar soft and pliable material suitable for human use. Outer portion 110 ensures that a smooth and atraumatic surface is provided for contact with the patient's skin. Main body 102 further includes an inner portion 112 that is formed of a more rigid material that has sufficient stiffness to maintain its shape and provide the necessary structural support and physical pressure on the patient's ear to allow the ear to remodel itself. At the same time, inner portion 112 is flexible enough that it is capable of being molded or shaped during implementation. Inner portion 112 may comprise any suitable element that is sufficiently rigid and bendable for these purposes, such as a flexible wire, filament, wire mesh or the like, and may comprise any suitable material, such as stainless steel, tungsten, aluminum, polymers or the like.

Inner portion 112 preferably extends along substantially the entire length of main body 102 of corrective component 100. In certain embodiments, inner portion 112 may curve back and pass through at least a portion of upper flange 108(*a*) to provide further support for upper flange 108(*a*). In other embodiments, inner portion 112 may also extend through a portion of lower flanges 108(*b*) and 108(*c*). Although inner portion 112 is shown as a substantially continuous, single component, the invention is not limited to this configuration. For example, inner portion 112 may comprise a plurality of separate components embedded at different locations within corrective component 100.

Main body 102 may be provided with a preformed shape corresponding to a desired shape of a normal human ear. Alternatively, main body 102 may be molded or shaped during implementation. For example, inner portion 112 of main body 102 is bendable and moldable, and able to maintain its shape after molding, such that the physician can sculpt the main body 102 of the corrective component 100 into the desired ear shape on the patient's ear. This design also allows for incremental shaping, since the physician would have the ability to shape the main body 102 incrementally over a time period to incrementally match the patient's ear to the shape of the model external ear. This feature would be especially helpful in cases of severe deformity or where the deformities may exist in distinct separate locations on the patient's ear.

In certain embodiments, corrective component 100 may include one or more magnets 114 embedded into outer portion 110, preferably within one or more of the flanges 108*a*, 108*b* and/or 108*c*. Magnets 114 serve to facilitate the temporary alignment of corrective component with an attachment element 140 (discussed in further detail below and shown in FIGS. 3A-3D). At least one pair of magnets having opposite polarity (i.e., +/− poles) may be used to form a magnetic connection between attachment element 140 and corrective component 100 during installation. Of course, more than one pair of magnets may be utilized, depending on the size of the main body 102.

Magnets 114 may take on any suitable shape and/or size effective to maintain the main body 102 in position relative attachment element 140. While the magnets 114 are shown as being circular, it is understood that the magnets may be elongate bars, oval, square, rectangular, or any other shape. Additionally, the magnets 114 themselves are not limited to a single magnetic body, and may be provided as magnetic material or magnetic fragments or filaments embedded within, or woven into, a material to create a magnetic-embedded material, weave or fabric. For example, magnetic filaments may be embedded within the main body 102 to achieve the same desired result. Of course, while magnets are described and shown, it is understood that other alignment mechanisms may also be employed, such as for example, medical grade adhesives or temporary glues, surgical tapes, Velcro or hook and loop materials, and other such known skin attachment mechanisms. For example, it is also possible to utilize a dovetail, or male-female grooved connection. It is further understood that a combination of alignment mechanisms may also be used together, such that magnets along with surgical tape may be used together, if so desired. The attachment mechanisms should ideally be strong enough to temporality align corrective component 100 with attachment element 140 during installation of the device (discussed in more detail below).

Figures 3A, 3B, 3C, 3D:
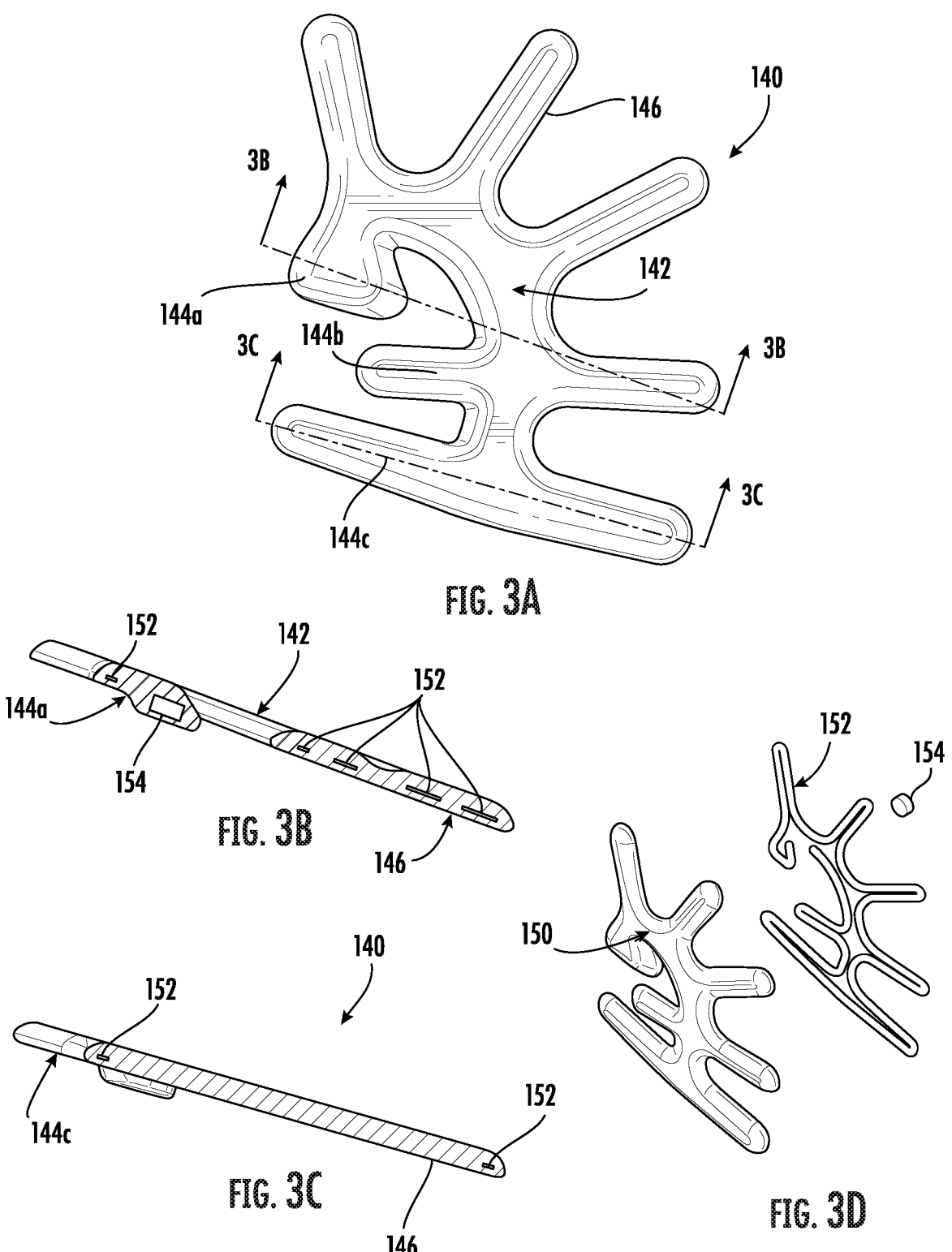
FIG. 3A is a front view of an attachment element for the corrective component of FIG. 2A and/or FIG. 4A.
FIG. 3B is a cross-sectional view of the attachment element of FIG. 3A taken along lines 3B-3B.
FIG. 3C is a cross-sectional view of the attachment element of FIG. 3A taken along lines 3C-3C.
FIG. 3D is an exploded view of the attachment element of FIG. 3A.

FIGS. 3A to 3D illustrate various views of attachment element 140. In particular, FIG. 3A shows a front view of the attachment element 140, FIGS. 3B and 3C show cross-sectional views along lines 3B-3B and 3C-3C, respectively, while FIG. 3D illustrates an exploded view. As shown, attachment element 140 includes a main body 142 with an arcuate shape that generally corresponds with the shape of main body 102 of corrective component 100 (i.e., with the shape of upper helix 6*a* of the patient's ear). Attachment element 140 further comprises one or more inner flanges or projections 144 and one more outer fingers or projections 146.

Figures 10A, 10B, 10C:
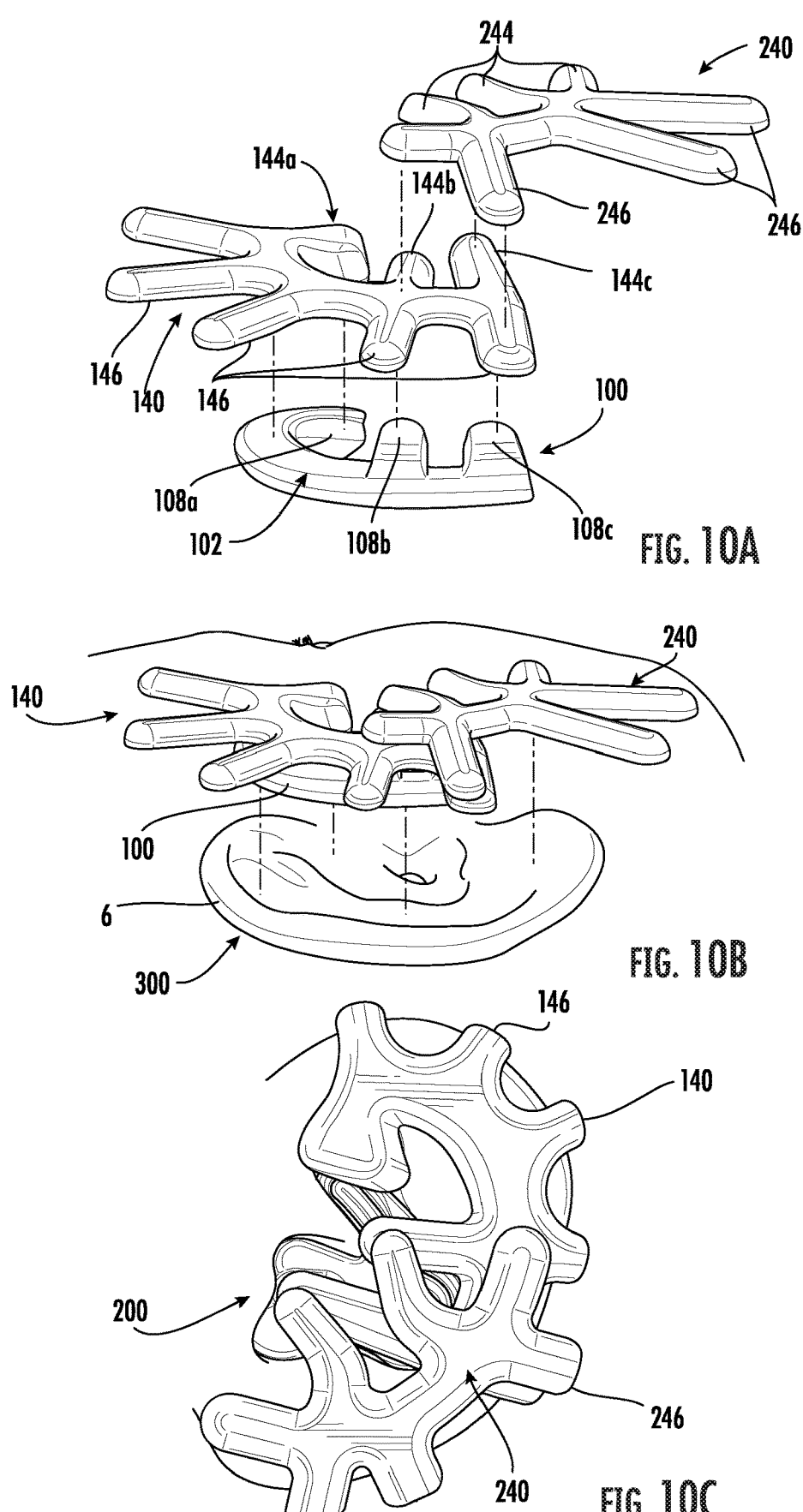
FIGS. 10A and 10B illustrate the alignment of the first and second attachment elements of FIGS. 3A and 5A with the corrective component of FIG. 2A and an exemplary human ear.

Inner flanges 144 are preferably shaped to generally correspond to the shape of flanges 108 of corrective component 100 (see FIG. 10A). In one exemplary embodiment, attachment element 140 includes an upper flange 144*a* that generally corresponds in shape with upper flange 108*a* of corrective component 100, and lower flanges 144*b* and 144*c* that define elongate fingers that generally correspond with the shape of lower flanges 108*b* and 108*c*. Of course, it will be recognized that other configurations are possible. For example, attachment element 140 may include any combination of inner flanges 144*a*, 144*b*, 144*c* (i.e., one or more of them) or it may contain inner flanges with entirely different shapes and configurations, such as square, rounded, oval, rectangular and the like.

Figure 6B:
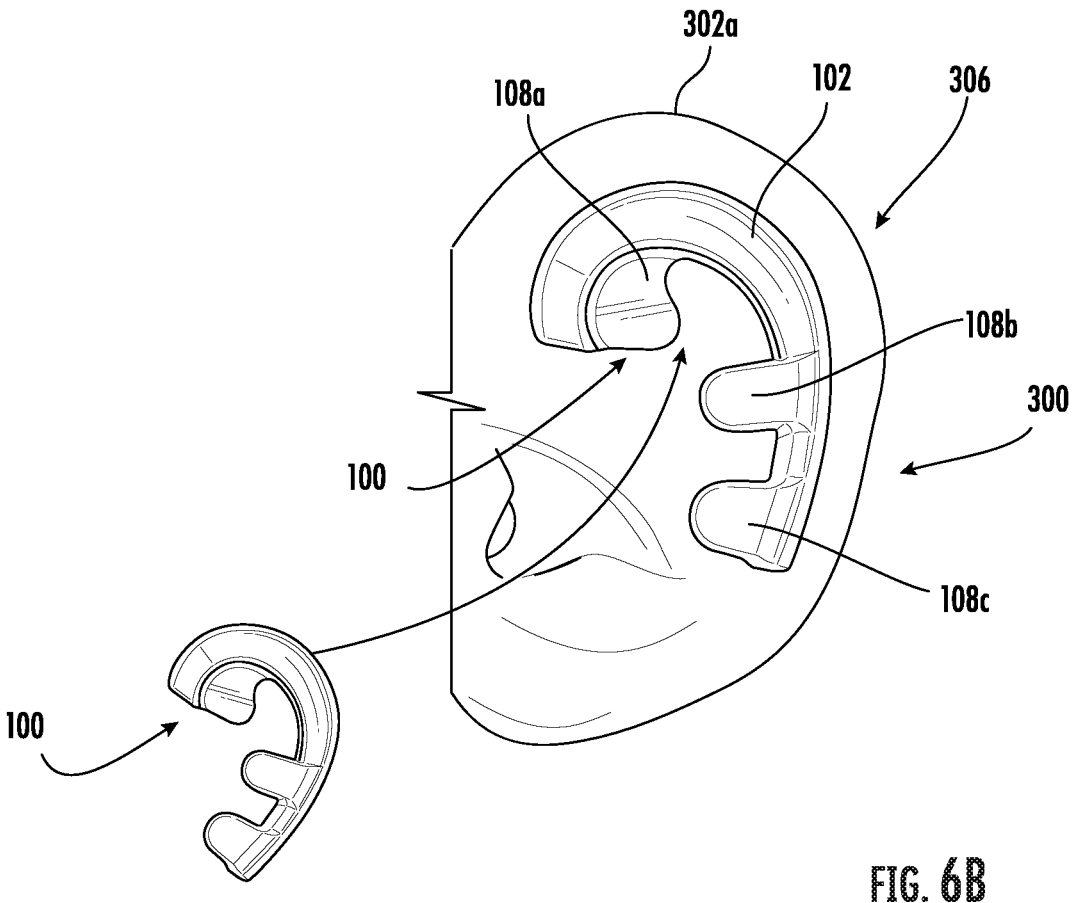
Figure 6C:
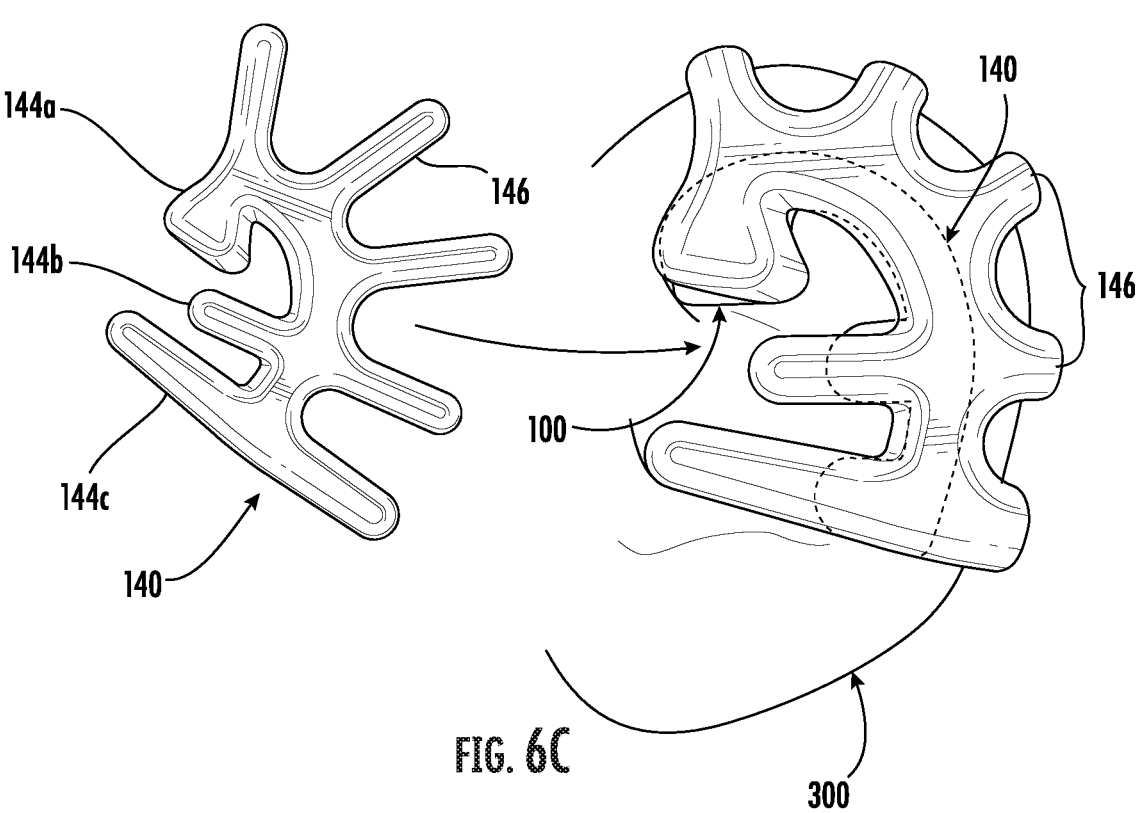
Figure 6D:
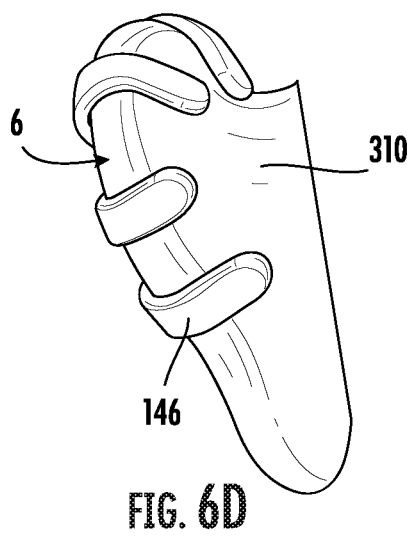

Outer flanges 146 are shaped and designed to wrap around the helix 6 of the ear 2 to hold attachment element 140 and corrective component 100 in place (see FIGS. 6C and 6D). In one exemplary embodiment, outer flanges 146 comprises elongate fingers that extend substantially perpendicular to main body 142. Outer flanges 146 have a length selected such that the flanges 146 may wrap around helix 6 to the rear surface of the ear, as shown in FIGS. 6C and 6D. Although five outer flanges are shown in the drawings, it should be recognized that attachment element 140 may comprise any suitable number of outer flanges in order to secure corrective component 100 in place (i.e., preferably around 2 to 10 flanges, more preferably between about 3 to 6).

As shown in FIG. 3D, main body 142 preferably comprises an outer portion 150 that comprises a flexible, soft and conformable material, such as medical grade silicone, polymer, plastic, polymeric blend, or similar soft and pliable material suitable for human use. Main body 142 further includes an inner portion 152 that is formed of a more rigid material that has sufficient stiffness to maintain its shape and provide the necessary structural support and physical pressure on the patient's ear to hold attachment element 140 against the ear 2. At the same time, inner portion 152 is flexible enough that it is capable of being wrapped around helix 6. The inner portion 152 may include one or more flexible wires, filaments, wire mesh or the like, which is embedded within the main body 142. The metal wires or filaments 152 may extend around the main body 142 along its spine, as illustrated in FIG. 3D. However, it is understood that the metal wires or filaments 152 may be located anywhere along the length of the main body 142, such as for example, positioned around the entire surface or at a discrete portion of the main body. The metal wires 152 allow the main body 142 to be bent to a desired shape, while maintaining this shape after manipulation by the physician.

In an exemplary embodiment, inner portion 152 is a continuous metal wire or filament that extends along main body 142 and into each of inner and outer flanges 144, 146. This configuration ensures that flanges 144, 146 have sufficient rigidity to maintain their shape after being bent or otherwise molded into position. Of course, those of skill in the art will recognize that other configurations are possible. For example, inner portion 152 may comprise multiple components or elements embedded within outer portion 150. These multiple components may be attached to each other, or they may be detached from each other. For example, the inner portion may comprise single metal wires or filaments extending through at least a portion of each flange 144, 146 and a separate metal wire extending through at least a portion of main body 152.

Attachment element 140 may further include one or more magnets 154 embedded within outer portion 150. As shown, magnets 154 are preferably located in one or more of the inner flanges 144 such that they align with magnets 114 of corrective component 100. The magnets 114 may be embedded within the flanges 144, or held within pockets or cutouts formed in the flanges 144. Additionally, similar to the description of magnets 114 above, the magnets 154 themselves are not limited to magnetic disc bodies, and may be provided as magnetic material or magnetic fragments or filaments embedded within, or woven into, a material to create a magnetic-embedded material, weave or fabric. For example, magnetic filaments may be embedded within outer portion 150 to achieve the same desired result. In one embodiment, the magnetic material for making this magnetic connection may be the metal wires 152, and therefore no separate magnetic element such as magnet 154 is necessary. As discussed in further detail below, magnets 114 and 154 provide sufficient attraction between flanges 108 and flanges 144 to facilitate alignment of corrective component 100 and attachment element 140 during installation.

Figure 4A:
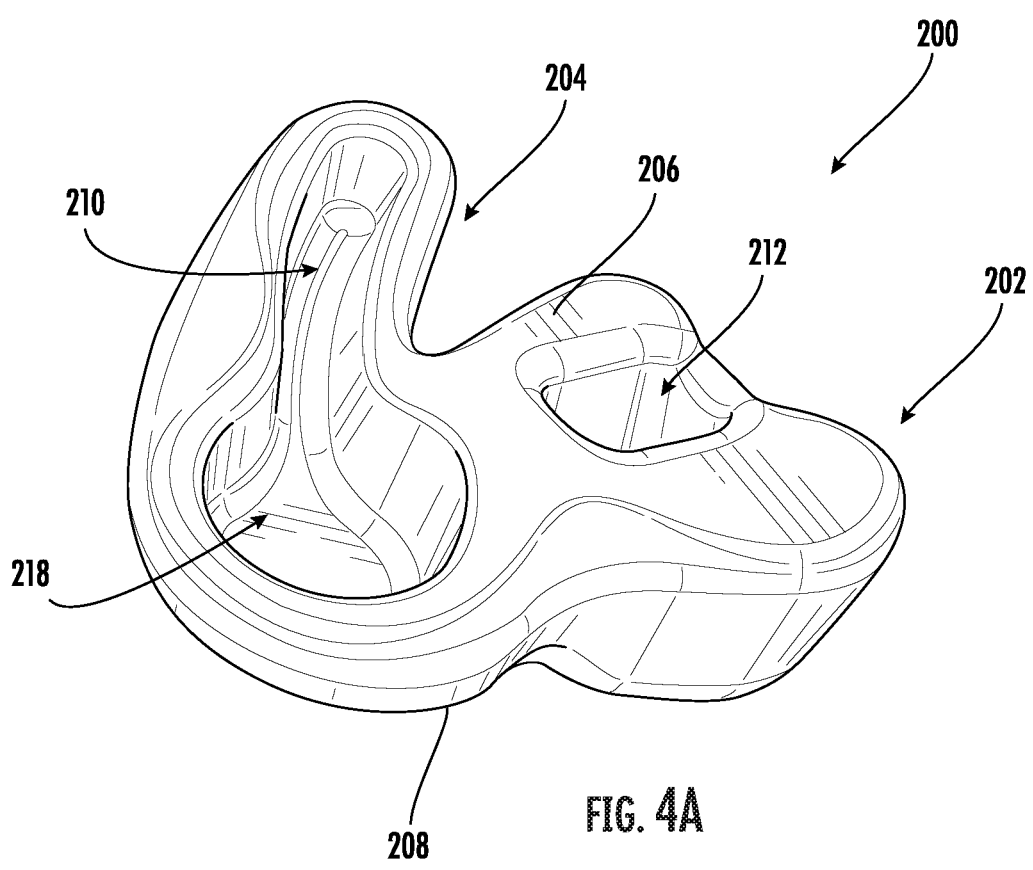
FIG. 4A is a perspective view of a corrective component for a conchal bowl of a human ear according to the present disclosure.
Figure 4B:
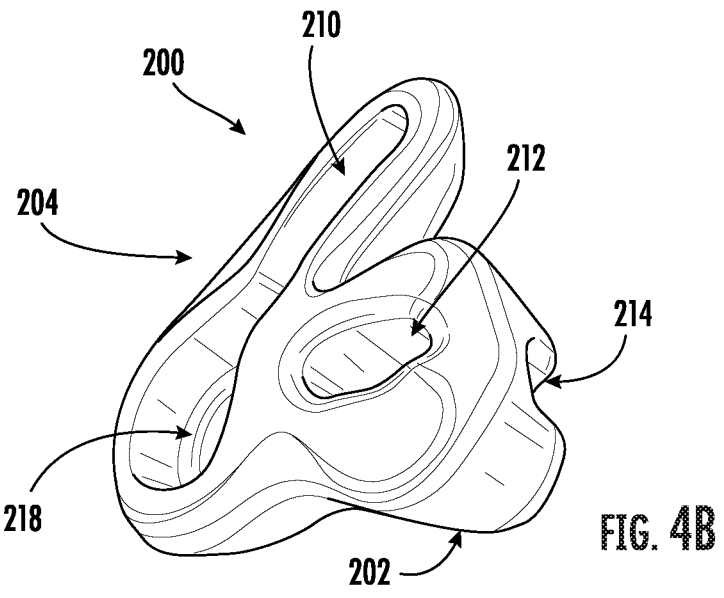
FIG. 4B is another perspective view of the corrective component of FIG. 4C is a front view of the corrective component of FIG. 4A.
Figure 4F:
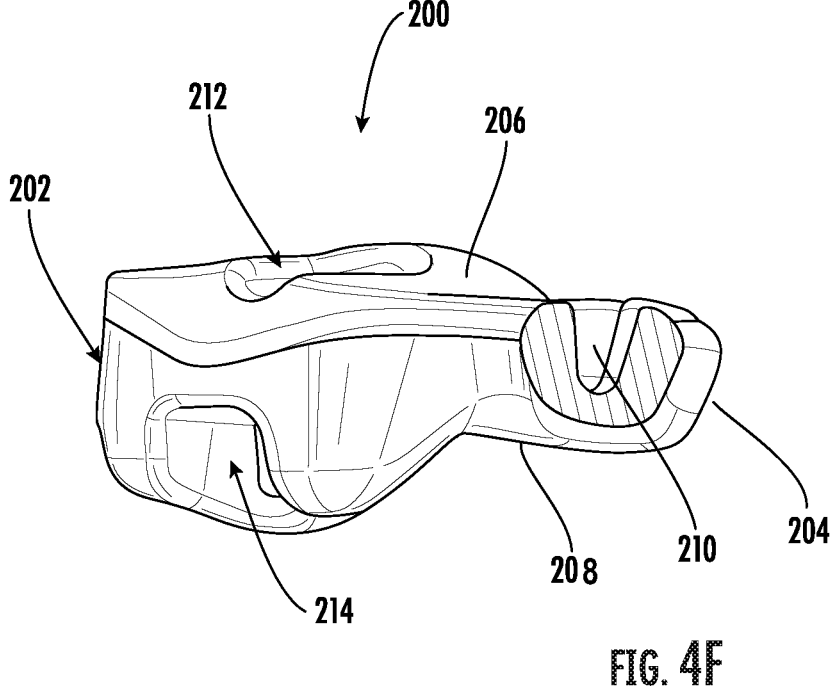
FIG. 4F is a cross-sectional view of the corrective component of FIG. 4C taken along lines 4F-4F.

FIGS. 4A to 4E illustrate various views of another exemplary embodiment of a corrective component 200 of the present disclosure. FIGS. 4A and 4B show perspective views of the corrective component 200, while FIG. 4C shows a front view and FIGS. 4D-4F show cross-sectional views taken along lines 4D-4D, 4E-4E and 4F-4F, respectively.

Corrective component 200 is configured as a conchal bowl insert, having a main body 202 and a stem 204 extending therefrom. The main body 202 is generally dimensioned to fit near or against the cavum 22 while the stem 204 has an elongate, slightly curved, shape generally configured to fit near or against the cymba 20 (or between the cymba 20 and the antihelix), which collectively form the concha or conchal bowl 24 (see FIGS. 7A and 7B). Corrective component 200 helps to mold the conchal bowl by flattening a vertical or horizontal conchal crus and often widening a tight conchal bowl during use.

Main body 202 and stem 204 of corrective component 200 include a first surface 206 and a second opposing surface 208. In certain embodiments, stem 204 further includes a cavity 210 in first surface 206. Cavity 210 is preferably a substantially elongate channel that extends through stem 204 and opens up into a chamber 218 having a generally circular cross-section. As shown in FIG. 4E, cavity 210 extends from first surface 206 into stem 204, but not completely through to second surface 208. Cavity 210 functions to provide additional flexibility to stem 204 such that it can be deformed slightly to fit within the conchal bowl of an infant ear. Cavity 210 also allows stem 204 to deform slightly during movement of the infant's ear, thereby providing more comfort and less trauma during use.

In certain embodiments, main body 202 includes an opening or hole 214 that extends completely through main body 202 from first surface 206 to second surface 208. Opening 214 provides a passage through corrective component 200 for sound waves to pass therethrough, allowing the patient to hear sounds while component 200 is installed. As shown in FIG. 7B, opening 214 is configured for positioning near, or over, the ear canal of the patient to facilitate passage of sounds waves through opening 214 and into the ear canal. In certain embodiments, opening 214 may be formed within a larger cavity 212 in first surface 206 of main body 200. Cavity 212 provides an acoustic chamber around opening 214 to enhance the passage of sound waves therethrough.

Corrective component 200 preferably comprises a flexible, soft and conformable material, such as medical grade silicone, polymer, plastic, polymeric blend, or similar soft and pliable material suitable for human use. Similar to other embodiments, corrective component may further include an inner portion (not shown) that is formed of a more rigid material that has sufficient stiffness to maintain its shape and provide the necessary structural support and physical pressure on the patient's ear to allow the ear to remodel itself.

FIGS. 5A to 5D illustrate a second attachment element 240 that may be used with corrective component 100, with corrective component 200, or with both of them in combination. As shown, second attachment element 240 includes a main body 242 with an arcuate shape that generally corresponds with the shape of descending helix 6b of the ear. Second attachment element 240 further comprises one or more inner flanges or projections 244 and one more outer flanges or fingers 246. Inner flanges 244 are preferably shaped to generally correspond to certain portions of first attachment element 140, corrective components 100, 200 and/or the patient's inner ear (see FIG. 9B). Outer flanges 246 are shaped and designed to wrap around the helix 6 of ear 2 to hold attachment element 240 and corrective component(s) 100 or 200 in place (see FIG. 9C).

Figures 5A, 5B, 5C, 5D:
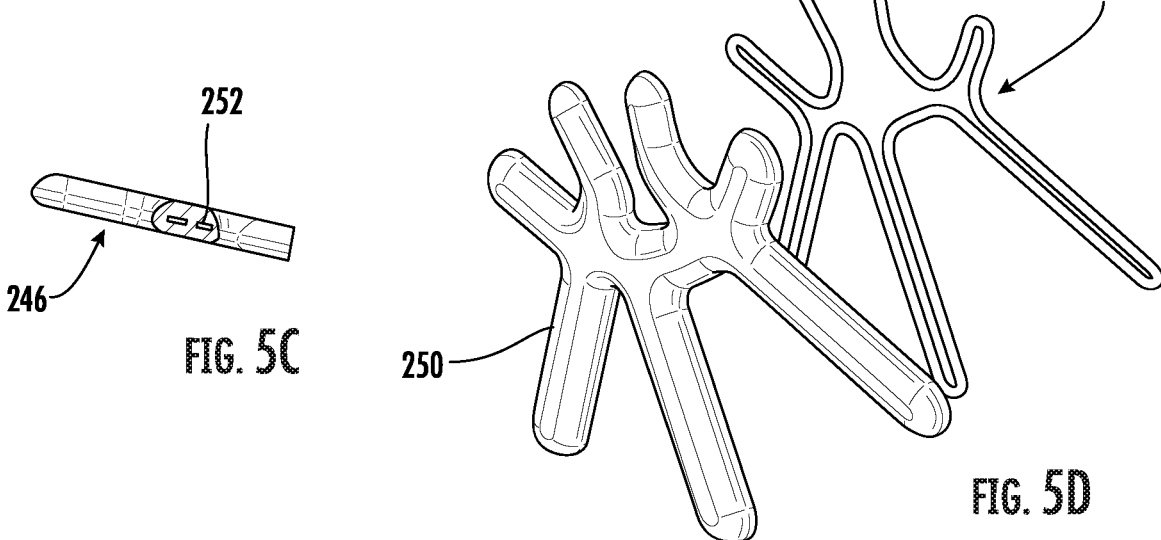
FIG. 5A is a front view of a second attachment element for the corrective components of FIGS. 2A and/or 4A.
FIG. 5B is a cross-sectional view of the second attachment element of FIG. 5A taken along lines 5B-5B.
FIG. 5C is a cross-sectional view of the second attachment element of FIG. 5A taken along lines 5C-5C.
FIG. 5D is an exploded view of the second attachment element of FIG. 5A.

As shown in FIG. 5D, main body 242 preferably comprises an outer portion 250 that comprises a flexible, soft and conformable materials, such as medical grade silicone, polymer, plastic, polymeric blend, or similar soft and pliable material suitable for human use. Main body 242 further includes an inner portion 252 that is formed of a more rigid material that have sufficient stiffness to maintain its shape and provide the necessary structural support and physical pressure on the patient's ear to hold second attachment element 240 against the ear 2. At the same time, inner portion 252 is flexible enough that it is capable of being wrapped around helix 6, such as a flexible wire, wire mesh or the like.

Similar to previous embodiments, inner portion 252 may comprise a continuous metal wire or filament that extends along main body 242 and into each of inner and outer flanges 244, 246. This configuration ensures the flanges 244, 246 have sufficient rigidity to maintain their shape after being bent or otherwise molded into position. Of course, other configurations are possible. For example, inner portion 252 may comprise multiple components or elements embedded within outer portion 250. These multiple components may be attached to each other, or they may be detached from each other. For example, the inner portion may comprise single wires or filaments extending through at least a portion of each flange and a separate wire extending through at least a portion of main body 252.

Attachment element 240 may further include one or more magnets (not shown) embedded within outer portion 250. The magnets may be located in one or more of the inner flanges 244 such that they align with magnets 114 of corrective component 100 or magnets 154 of first attachment element 140. As discussed above, the magnets are designed to provide sufficient attraction between attachment elements 140, 240 and corrective components 100, 200 to facilitate proper alignment of second attachment element 240 during installation.

Referring now to FIGS. 6A-6D, a method for installing corrective component 100 in, or on a surface of, a patient's external ear 300 will now be described. FIG. 6A illustrates an exemplary deformed ear 300 having an upper surface 302 of the helix 6 that is deformed. In particular, upper surface 302 droops downward from the ideal location (shown as surface 302a in dotted lines). One of the goals of the procedure is to remodel the deformed ear 300 such that upper surface 302 is reshaped into model surface 302a.

Referring to FIG. 6B, corrective component 100 is first positioned at least partially in contact with the inner surface of the external ear so that main body 102 is adjacent helix 6 (see 6B). In some embodiments, corrective component is designed such that it will nest within helical rim 8 of the ear and remain in place without any additional means of attaching it thereto. In other embodiments, one or more attachment elements may be used to further secure corrective component 100 to the patient's ear.

As shown in FIG. 6C, first attachment element 140 may be positioned against corrective component 100 such that inner flanges 144 generally align with inner flanges 108. In some embodiments, opposing polarity magnets 114 and 154 can be used to facilitate this alignment. Once attachment element 140 is in position, outer fingers 146 are wrapped around the helix 6 of the ear 300. Outer fingers 146 of attachment element 140 have sufficient rigidity to remain in place around the rear side 310 of the helix 6 (see FIG. 6D). Attachment element 140 is substantially atraumatic to the ear, thereby increasing the comfort for the patient, while still holding corrective component 100 in place during a time period of use sufficient to correct the deformity.

Figure 7A:
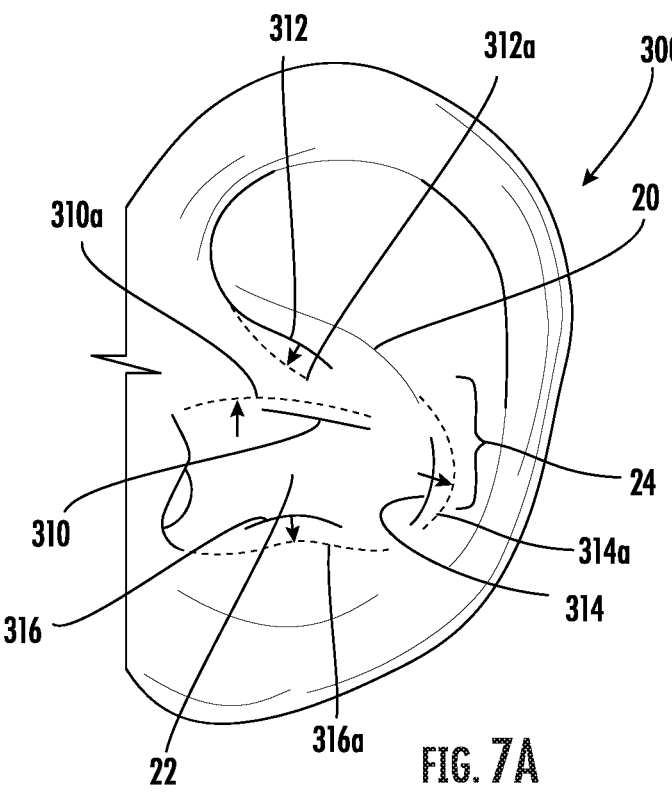
FIGS. 7A and 7B illustrate the placement of the corrective component of FIG. 4A near, or against, a conchal bowl of an exemplary human ear according to the present disclosure.
Figure 7B:
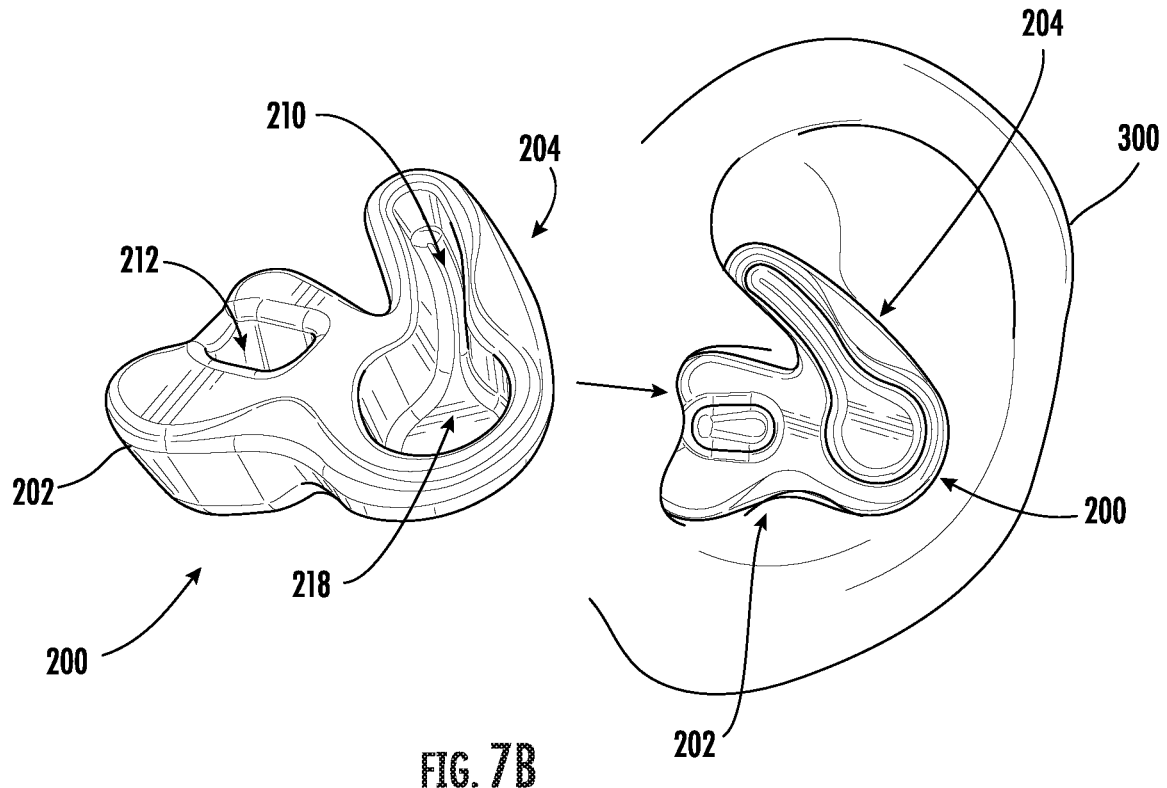

FIGS. 7A and 7B illustrate a method of installing corrective component 200 into the conchal bowl 24 of a patient's ear 300. FIG. 7A shows the auricle of an exemplary human ear with the concha cymba 20 and cavum 22, which collectively can be generally referred to as the concha, or conchal bowl 24. FIG. 7A illustrates deformed surfaces 310, 312, 314 and 316. The goals for the conchal bowl remodeling is often to change the dimensions of the conchal bowl, widen a conchal bowl and/or to correct and flatten a conchal crus or extra band of cartilage in the conchal bowl. In certain embodiments, some or all of these surfaces are displaced to the positions shown by the dotted lines, respectively, 310a, 312a, 314a and 316a, thereby expanding the size of the conchal bowl 24.

Referring now to FIG. 7B, second corrective component 200 is substantially shaped to fit within the conchal bowl 24 with main body 202 generally residing in, or around, the cavum 22 and stem 204 positioned near, or along, the cymba 20. Elongate channel 210 and chamber 218 provide a certain degree of flexibility to the walls of stem 204 during placement to minimize trauma to the patient. In addition, channel 210 and chamber 218 allow for some displacement of stem 204 during remodeling. Hole 214 is positioned near, or directly over, the ear canal to allow sound waves to pass therethrough such that the patient may hear sounds while corrective component 200 is in place.

In some embodiments, the shape of second corrective component 200 allows it to remain in place within the conchal bowl 24 for a sufficient period of time to reshape the conchal bowl 24 and correct the deformity. In other embodiments, one or more attachment elements 140, 240 may be used to anchor corrective component 200 in place.

Figures 8A, 8B, 8C, 8D:
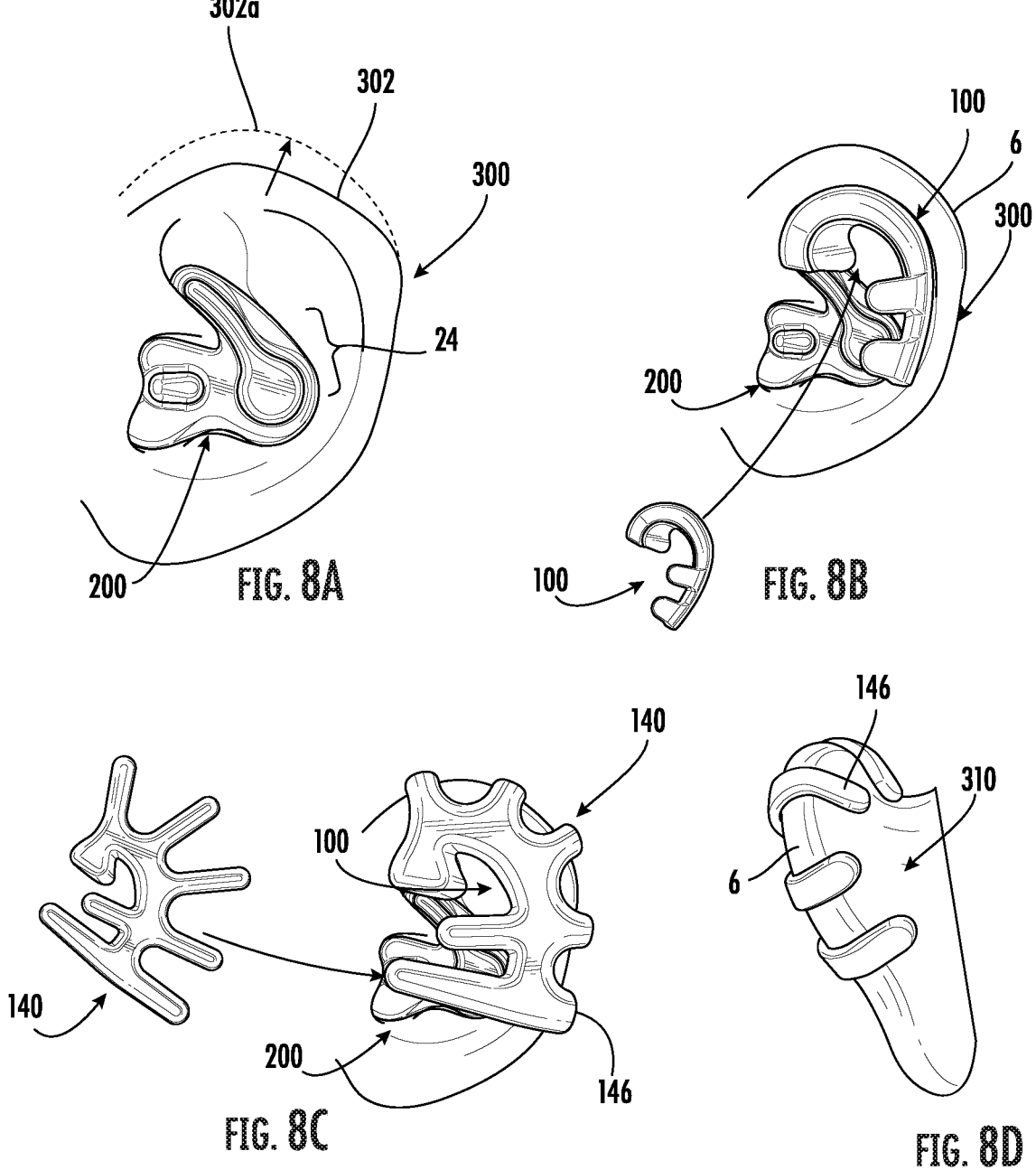
FIGS. 8A-8D illustrate the placement of the corrective components of both FIGS. 2A and 4A and the attachment element of FIG. 3A on target surfaces of an exemplary human ear according to the present disclosure.

FIGS. 8A-8D illustrate a method of installing first and second corrective components 100, 200 within, or against, a patient's ear. As shown in FIG. 8A, second corrective component 200 is first positioned within the conchal bowl 24, as described above. First corrective component 100 is then positioned at least partially in contact with the inner surface of the ear so that main body 102 nests within helical rim 8 (FIG. 8B). Note that flanges 108 of corrective component 100 may overlap with certain portions of corrective component 200 to provide additional security for both components. In some embodiments, corrective component 200 may include magnets (not shown) configured to be attracted to magnets 114 within corrective component 100 to facilitate proper alignment between these two components.

As shown in FIG. 8C, attachment element 140 may then be aligned with corrective components 100, 200, as discussed above. Attachment element 140 may be designed to align only with first corrective component 100, or with both components 100, 200. In addition, magnets 154 on attachment element 140 may be designed to facilitate alignment with either or both components 100, 200. Once attachment element 140 is properly positioned, outer fingers 146 are wrapped around helix 6 of the ear to secure all of the components in place (see FIG. 8D). In some embodiments, second attachment element 240 may also be aligned with first attachment element 140 and/or one or both of corrective components 100, 200.

Figures 9A, 9B, 9C:
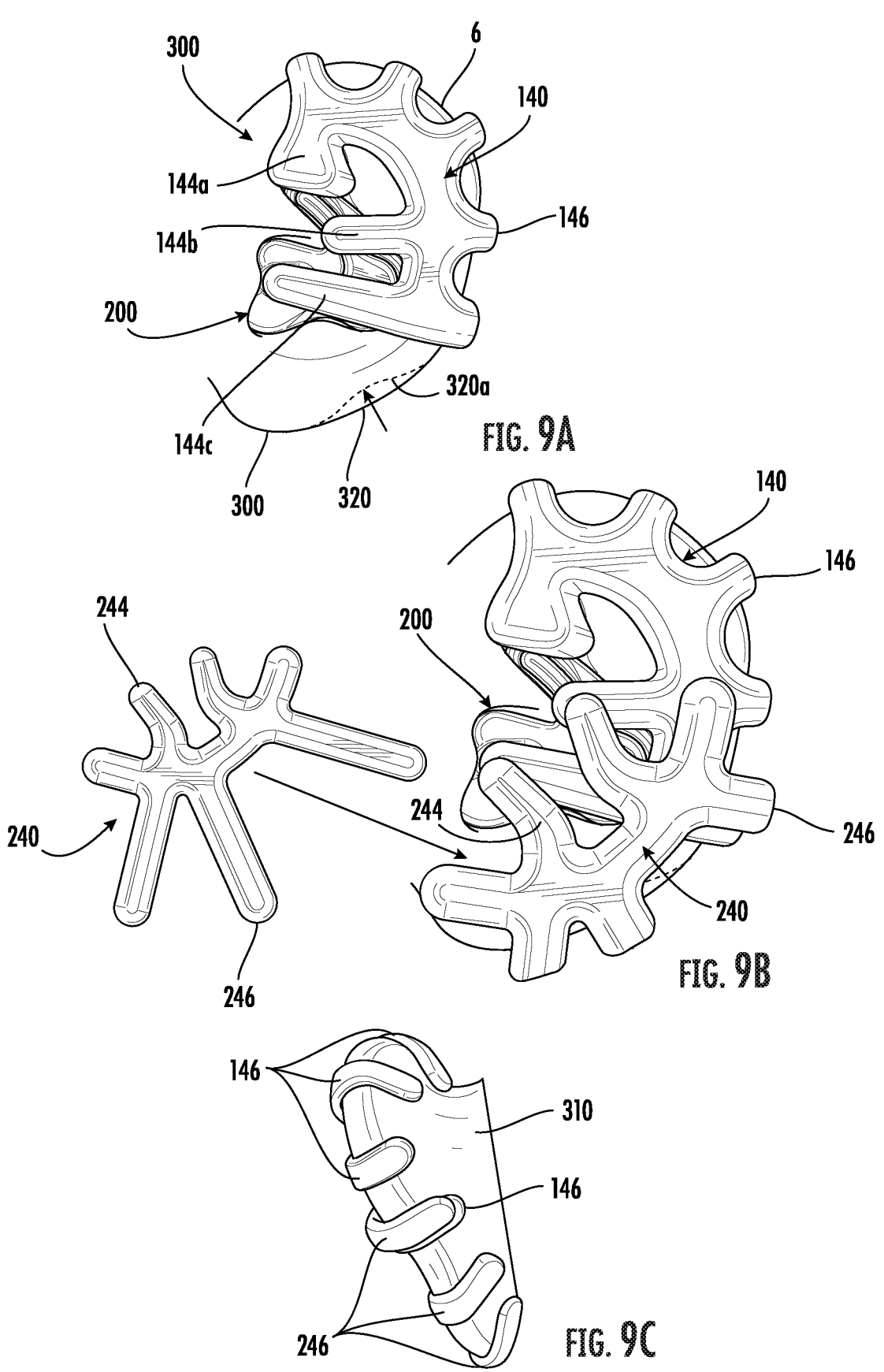
FIGS. 9A-9C illustrates the placement of the second attachment element of FIG. 5A, together with the attachment element of FIG. 3A and the corrective component of FIG. 4A, on a target surface of an exemplary human ear according to the present disclosure.

FIGS. 9A-9C illustrate yet another embodiment wherein second corrective component 200 is used in conjunction with both attachment elements 140, 240. In this embodiment, corrective component 100 is not shown, although it could be employed as discussed above. Similar to previous embodiments, corrective component 200 is first positioned within conchal bowl 24 (FIG. 9A). Attachment element 140 is then positioned over corrective component 200 and wrapped around helix 6, as described above. As shown in FIG. 9B, second attachment element 240 is then positioned over, and in alignment with, attachment element 140 and corrective component 200. Finally, outer fingers 246 of attachment element 240 are then wrapped around helix 6 and lobule of the ear to provide further security to the entire corrective apparatus (as shown in FIG. 9C).

FIGS. 10A-10C illustrate yet another embodiment wherein both attachment elements 140, 240 are employed to secure first corrective component 100 in place. As shown in FIG. 10A, inner flanges 144 of attachment element 140 are substantially aligned with inner flanges 108 of corrective component 100. Second attachment element 240 is then aligned with first attachment element 140, as shown. Referring now to FIG. 10B, the entire corrective apparatus is then positioned against the inner ear such that corrective component 100 resides inside of the helical rim 8. Finally, outer fingers 146 and 246 of attachment elements 140, 240 respectively, are wrapped around the helix 6 to secure the entire corrective apparatus in place (see FIG. 10C). Although FIGS. 10A-10C illustrate the alignment of the components prior to placement against the patient's ear, it will be recognized that each component may be placed against the ear sequentially, as discussed in previous embodiments.

FIGS. 11A and 11B illustrate another exemplary embodiment of a corrective apparatus 400 of the present disclosure.

Figure 13A:
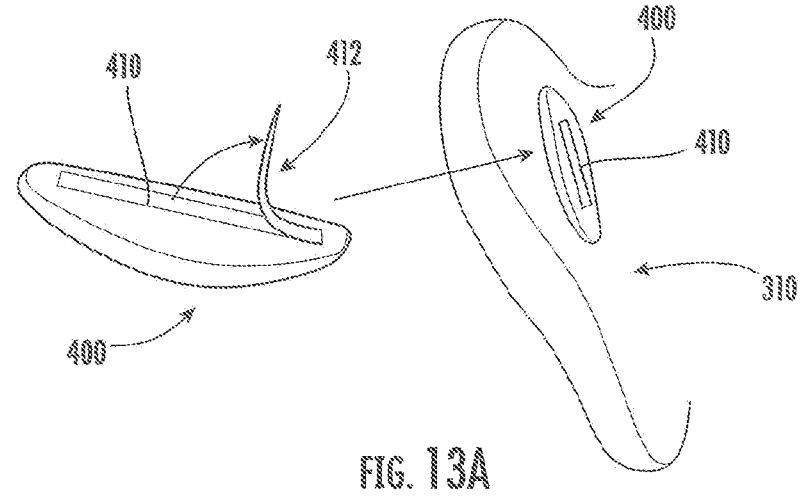
FIGS. 13A-13C illustrate the placement of the corrective component of FIG. 11A against a rear surface of the human ear.

Corrective apparatus 400 is configured to attach to a rear surface of the ear to help form an absent superior limb of the antihelix. In certain embodiments, corrective apparatus 400 includes a main body 402 with an upper generally convex surface 404 configured for contacting an outer surface 310 of the patient's ear 2 (see FIG. 13A), and a lower, substantially flat surface 406. Flat surface 406 may include an adhesive surface 410 for securing corrective apparatus 400 to one or more attachment elements or to a portion of the patient's ear. A removable release liner 412 may also be positioned on adhesive surface 410.

In an exemplary embodiment, corrective component 400 may be held in place by the phalanges of the helical rim holder. In other embodiments, corrective component 400 may be used in combination with a cryptotia clip 440 (described below with reference to FIGS. 12A-12E) or another attachment element (such as those described above). Similar to the other corrective apparatuses previously described, attachment mechanisms such as magnets or magnetic elements such as magnetic embedded fibers within the device (not shown) may also be utilized. For example, at least a pair of magnets of complementary polarity may be employed with the corrective apparatus 400 to create a magnetic connection between corrective apparatus 400 and a separate attachment element to ensure that the corrective apparatus 400 remains in position during use.

Referring now to FIGS. 12A-12E, another embodiment of a corrective apparatus 440 will now be described. Corrective apparatus 440 may be configured as an ear clip that is intended to treat "hidden" ear deformities or cryptotia. Corrective apparatus 440 may be configured for use at the root of the helix of the ear 2. In some patients, this portion of the ear 2 may be hidden under the scalp skin, in a condition called cryptotia.

Figure 13B:
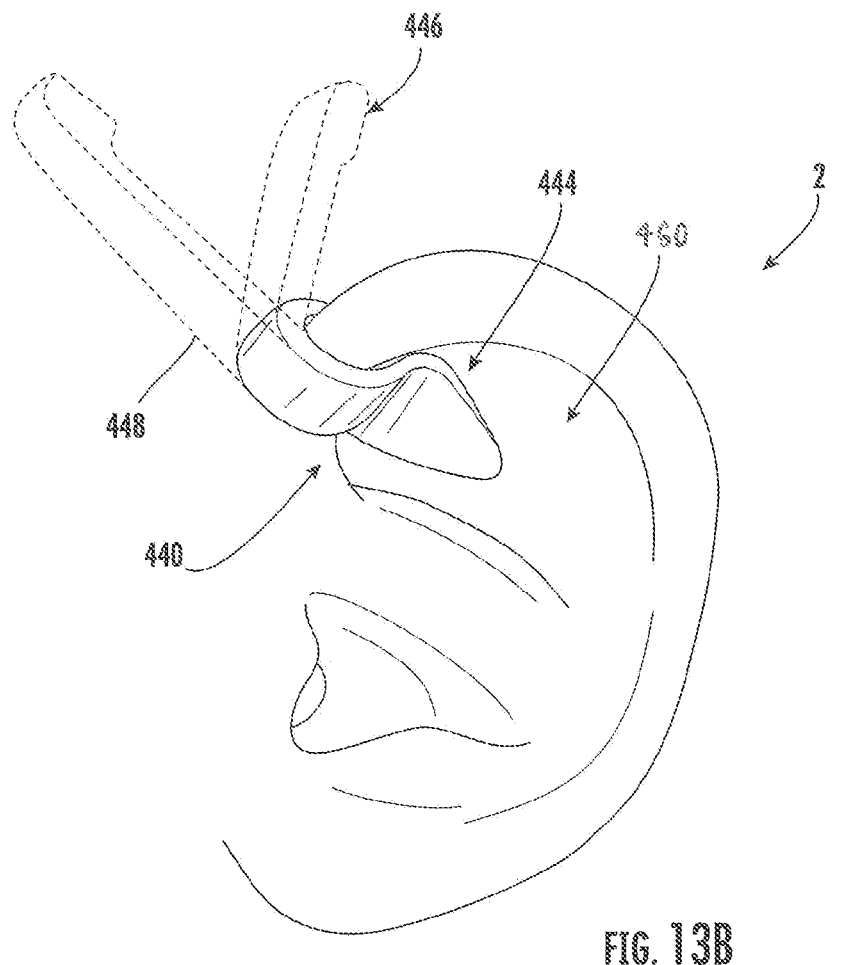
Figure 13C:
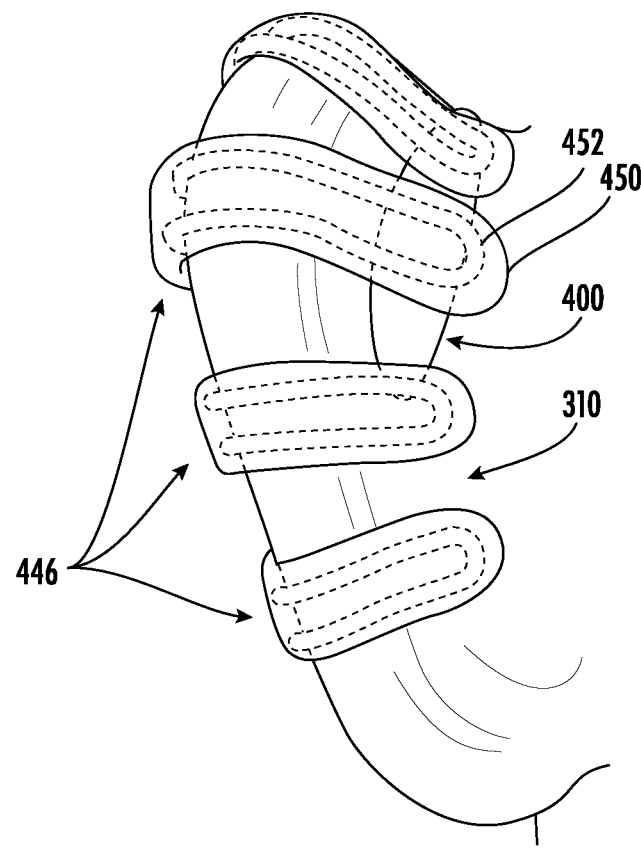

FIG. 12A illustrates an open view of a cryptotia clip, which is a corrective apparatus 440 that clips over the ear 2 (as shown in FIGS. 13B and 13C) and keeps a portion of the ear from slipping under the temporal scalp skin. As shown, corrective apparatus 440 comprises a main body 442 having an anterior portion 444, a posterior portion 446 and an elongate section 448 therebetween. As shown, anterior portion 444 is preferably shaped to fit against an inner surface 460 of the ear 2 underneath the helical rim 8. Elongate section 448 is designed to wrap around the helix 6 and posterior portion 446 is configured to contact the rear surface 310 of the ear 2. Posterior portion 446 may include an adhesive surface (not shown) for coupling to the rear surface of ear 2 or to the adhesive surface of another corrective apparatus or attachment element, such as the adhesive surface 410 of corrective apparatus 400.

Similar to previous embodiments, corrective component 440 may include an outer portion 450 that comprises a flexible, soft and conformable material, such as medical grade silicone, polymer, plastic, polymeric blend, or similar soft and pliable material suitable for human use (see FIG. 13C). Corrective component 440 further includes an inner portion 452 that is formed of a more rigid material that has sufficient stiffness to maintain its shape and provide the necessary structural support and physical pressure on the patient's ear to hold corrective component 440 against the ear 300. At the same time, inner portion 452 is flexible enough that it is capable of being wrapped around helix 6, such as a flexible wire, wire mesh or the like.

Referring to FIGS. 13B-13C a method of installing corrective component 440 against a patient's ear will now be described. As shown in FIG. 13B, anterior portion 444 of corrective component 440 is positioned snugly against the interior surface 460 of the patient's ear underneath the helical rim 8. The cryptotia clip is preferably designed to fit into the triangular fossa and hold the pinna in its corrected position. In cryptotia, the root of the helix and a portion of the superior helix is under the scalp skin and needs to be manually pulled from that position and held in the correct position for a duration of time to correct the deformity. Elongate portion 448 of corrective component 440 is then wrapped around the helix 6 such that posterior portion 446 can be positioned against the rear surface of the ear 2 (FIG. 13C).

It is understood that the corrective apparatus 400 may be used alone as a single corrective device, or in combination with other devices or systems described herein.

Figure 14A:
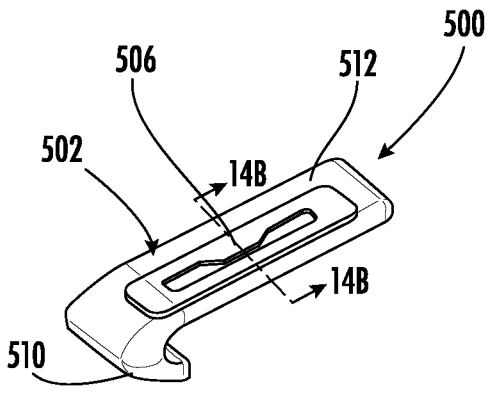
FIG. 14A illustrates a perspective view of another embodiment of an attachment element according to the present disclosure.
Figure 14B:
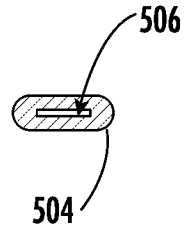
FIG. 14B illustrates a cross-sectional view of the attachment element of FIG. 14A taken along lines 14B-14B.
Figure 14C:
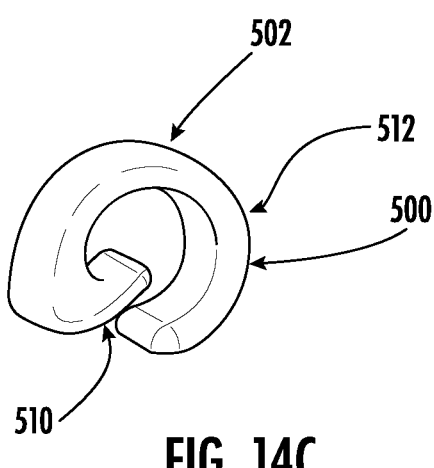
FIG. 14C illustrates the attachment element of FIG. 14A in a pre-formed configuration.

Referring now to FIGS. 14A-14C, another embodiment of an attachment element 500 for use with one of the corrective components of the present disclosure will now be described. As shown, attachment element 500 includes a main body 502 that includes an outer portion 504 and an inner portion 506. Similar to previous embodiments, outer portion 504 preferably comprises a flexible, soft and conformable materials, such as medical grade silicone, polymer, plastic, polymeric blend, or similar soft and pliable material suitable for human use. Inner portion 506 is formed of a more rigid material that have sufficient stiffness to maintain its shape and provide the necessary structural support and physical pressure on the patient's ear to hold second attachment element 500 against the ear 2 (see FIG. 15). At the same time, inner portion 506 is flexible enough that it is capable of being wrapped into a pre-formed shape for placement around helix 6 (see FIG. 14C).

As shown, main body 502 includes a curved anterior portion 510 and an elongate portion 512 that extends from anterior portion 510. Anterior portion 510 is preferably curved inwardly relative to elongate portion 512 such that it can be easily attached to the helical rim 8 of ear 2. Anterior portion 510 is also sized and shaped to engage a portion of the corrective component to align attachment element 500 with the corrective component. In certain embodiments, anterior portion 510 may be sized and shaped to press-fit against the corrective component to secure attachment element 500 to the corrective component. In one exemplary embodiment, attachment element 500 is designed for use with corrective component 100 (shown in FIGS. 2A-2E). In this embodiment, anterior portion 510 is designed to engage main body 102 of corrective component 100 and press main body 102 further into the recess formed in the ear under helical rim 8. This ensures that corrective component 100 remains in place for a sufficient length of time to correct the deformity and help round out the outer helical rim.

In other embodiments, anterior portion 510 may be engaged to the corrective component by advancing anterior portion 510 into a cavity, rim, channel or other recessed surface of the corrective component. Alternatively, anterior portion 510 may also include one or more magnets (not shown) and/or adhesive elements (also not shown) for providing temporary or permanent attachment to one of the corrective components described above.

Main body 502 is designed to be "pre-formed" such that elongate portion 512 is curved around into the position shown in FIG. 14C. This configuration allows the physician or caregiver to place attachment element 500 around the helix 6 of the ear 2 without having to significantly bend or deform main body 502, thereby providing an atraumatic placement of attachment element 500 around the patient's ear (discussed in more detail below).

Elongate portion 512 preferably has a length selected such that it can be placed entirely around the helix 6 of the ear 2. Elongate portion 512 also includes inner portion 506 which includes a more rigid material with sufficient stiffness to maintain its shape and sufficient flexibility to wrap around helix 6, as discussed previously.

Figure 15:
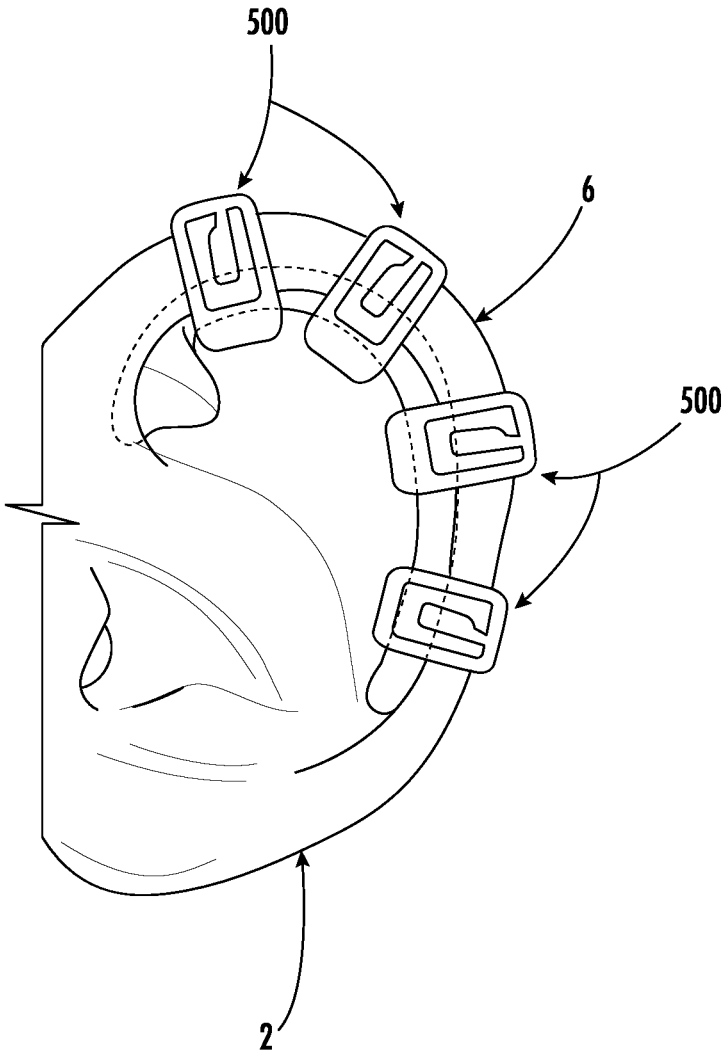
FIG. 15 illustrates the placement of a plurality of the attachment elements of FIGS. 14A-14C around the helix of the human ear.

Referring now to FIG. 15, one or more attachment elements 500 are employed to secure a corrective component (not shown) in place. Attachment elements 500 may be used to secure any of the corrective components of the present disclosure, or other corrective components that are not described herein. Attachment elements 500 may be used in lieu of, or in combination with, previously-described attachment elements 140 and/or 240.

As discussed above, the corrective component is first placed into the desired location in the patient's ear (e.g., corrective component 100 as shown in FIG. 6B). Anterior portion 510 of attachment element 100 is substantially aligned with, or engaged to, one of the surfaces of the corrective component. Anterior portion 510 is then placed around the inner portion of helical rim 8 and elongate portion 512 is placed around the helix 6 to secure the entire corrective apparatus in place. As discussed above, attachment element 500 has already been pre-formed such that elongate portion 512 is substantially in the shape required for placement around the helix. This reduces the trauma that may otherwise be experienced by the patient if elongate portion 512 were wrapped around the helix 6. After attachment element 500 has been placed into position as shown in FIG. 14C, elongate portion 512 may be bent or deformed slightly to more tightly secure it to the patient's ear.

One of the advantages of the embodiment shown in FIGS. 14A-14C is its versatility. One or more attachment element(s) 500 may be used in combination with one or more corrective component(s). In addition, attachment element(s) 500 may be placed into different positions around the helix 6 of the ear depending on the geometry of the individual patient's ear. Thus, attachment element(s) 500 can be placed only where pressure is needed to retain the corrective component. The specific areas where pressure may be needed will often vary with the geometry of the patient's ear. This allows the caregiver to choose where to apply pressure and in how many places the pressure should be applied. For example, in certain ears, only one or two attachment element(s) 500 may be required to sufficiently retain the corrective component in place. In other ears, three or more attachment element(s) 500 may be required.

Referring now to FIGS. 16A-16C, another embodiment of an attachment element 600 includes an outer portion 602 and an inner portion 604 similar to the above embodiments. Also, similar to the embodiment in FIGS. 14A-14C, attachment element 600 is configured to be "pre-formed" into a curved configuration for placement around helix 6 of the patient's ear 2 (see FIG. 16B). Attachment element 600 further includes a substantially triangular-shaped flange 620 extending inwardly from a main body 606. Flange 620 can be used to further align attachment element 600 with the corrective component (e.g., corrective component 100). In addition, flange 620 may be used with patients that are missing, or have a deformed, triangular fossa. The triangular fossa is the shallow depression in the anterior part of the top of the ear's auricle between the two crura (Crura of antihelix). The antihelix divides above and into the two crura forming the triangular fossa therebetween. Flange 620 is designed to fit into the area wherein the triangular fossa is normally located, thereby providing an index to align attachment element 600 with the corrective component.

While some of the corrective apparatuses of the present disclosure have been described thus far with embedded metal wires or filaments, the metal wires or filaments may be part of a metal mesh or a metal weave (not shown). The metal mesh or weave may be positioned at discrete locations on the main body of the corrective apparatus, or the metal mesh or weave may extend throughout the main body. Here, the metal wires or filaments form a metal mesh or weave that extends throughout the main body of the corrective apparatus.

Kits for correcting ear deformities in newborns and young infants can be provided which would include a set of corrective apparatuses similar to the ones shown and described herein, along with a user's guide. In one embodiment of a user's guide, the guide may take the form of a transparent template that may include an outline of a model human ear. The guide may be placed onto a photograph of a patient's ear. Using the line guides separating the various sections (e.g., A, B, C, and D) of the ear to be treated, the physician can identify which section(s) includes the deformity or deformities. The physician can then match the section(s) with the corresponding corrective apparatus(es) for that section(s). As a visual aid, these sections may also be colored for ease of use.

In an exemplary method of using the corrective apparatuses of the present disclosure, a physician could first select the appropriately sized and shaped corrective apparatus using the user's guide as described above, or by self-selecting the corrective apparatus from the set of apparatuses. Next, the physician can manipulate and bend the corrective apparatus to conform the shape of the corrective apparatus to a desired model ear shape. The conformed corrective apparatus can then be placed on the patient's ear for a time period to urge the patient's ear towards the desired model ear shape.

Although the corrective apparatuses and corrective systems of the present disclosure are described herein for use in newborns and young infants, it is understood that the corrective apparatuses and corrective systems may be equally applicable for use in older children as well as in adults who have external ear deformities. In addition, corrective components 100, 200, 400 of the present disclosure may each be used alone, in combination with each other or in combination with other ear components. One example of other corrective components that may be used in combination with the features of the present disclosure can be found in commonly-assigned co-pending International Patent Application No. PCT/US19/60952 to CORRECTIVE APPARATUS FOR DEFORMED EXTERNAL EAR, filed Nov. 12, 2019, the complete disclosure of which is hereby incorporated herein by reference for all purposes as if copied and pasted herein.

Corrective apparatuses and corrective systems of the present disclosure may be customized to a patient using 3D printing techniques. For example, the dimension(s) of the model external ear may match the dimension(s) of the deformed external ear (such as in length, width, size, and/or density, among others). The components of the corrective apparatus (such as the main body) may also be printed with a three dimensional printer. The three dimensional printer may use the model external ear as the blueprint for the corrective apparatus. The three dimensional printer may match a shape and dimension(s) of the model external ear (e.g., such as a size) while printing the corrective apparatus.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A corrective apparatus for treating a deformity of an external ear, comprising:

a corrective component shaped for insertion into a conchal bowl of the ear, the corrective component comprising a main body configured for placement against at least a portion of a cavum of the ear, the main body having a first, upper surface and a second, lower surface, the corrective component further including a stem extending at an angle from the main body and configured for placement against at least a portion of a cymba of the ear, the stem having a first, upper surface and a second, lower surface, wherein the stem includes a cavity extending from the first, upper surface but not through the second, lower surface, and wherein the cavity provides flexibility to the stem to allow deformation.

2. The corrective apparatus of claim 1, wherein the main body and the stem are configured to mold the conchal bowl of the ear.

3. The corrective apparatus of claim 2, wherein the corrective component is formed from a material comprising a silicone, polymer, plastic, or a blend thereof.

4. The corrective apparatus of claim 2, wherein the corrective component is bendable for movement into a position against the conchal bowl.

5. The corrective apparatus of claim 2, wherein the main body and the stem are configured to flatten a vertical or horizontal conchal crus of the ear.

6. The corrective apparatus of claim 2, wherein the main body and the stem are configured to widen the conchal bowl of the ear.

7. The corrective apparatus of claim 1, wherein the main body includes a cavity formed in the first, upper surface.

8. The corrective apparatus of claim 7, wherein the main body further comprises a hole extending from the second, lower surface to the cavity in the main body, wherein the hole is configured to be substantially aligned with an ear canal for passing sound waves through the main body to the ear canal.

9. The corrective apparatus of claim 8, wherein the cavity in the main body forms an acoustic chamber around the hole to enhance the passage of sound waves therethrough.

10. The corrective apparatus of claim 8, wherein the opening extending from the second, lower surface of the main body is smaller than the cavity of the main body.

11. The corrective apparatus of claim 1, further comprising an attachment element configured for placement around a portion of the external ear for securing the corrective component against the conchal bowl.

12. The corrective apparatus of claim 11, wherein the attachment element is configured for attachment to a portion of an outer skin surface of a head of the patient.

13. The corrective apparatus of claim 11, wherein the attachment element is configured to wrap around a helix of the ear.

14. The corrective apparatus of claim 11, wherein the attachment element comprises an adhesive.

15. The corrective apparatus of claim 1, wherein the cavity of the stem comprises a substantially elongate channel extending into a substantially circular chamber.

16. A corrective apparatus for treating a deformity of an external ear, comprising:

a corrective component shaped for insertion into a conchal bowl of the ear, the corrective component comprising a main body configured for placement against at least a portion of a cavum of the ear, the main body having a first, upper surface and a second, lower surface, the corrective component further including a stem extending at an angle from the main body so as to be configured for placement against at least a portion of a cymba of the ear, the stem having a first, upper surface and a second, lower surface, wherein the main body and the stem each comprise an outer portion configured for contacting a surface of the conchal bowl, and an inner portion within the outer portion, and wherein the outer portions of the main body and stem have a different stiffness than the inner portions of the main body and stem, wherein the stem includes a cavity extending from the first, upper surface but not through the second, lower surface, and wherein the cavity provides flexibility to the stem to allow deformation.

17. The corrective apparatus of claim 16, wherein the outer portions of the main body and stem are formed from a different material than the inner portions of the main body and stem.

18. The corrective apparatus of claim 16, wherein the inner portions of the main body and stem are stiffer than the outer portions of the main body and stem.

* * * * *